(12) United States Patent
Desrochers et al.

(10) Patent No.: US 8,147,302 B2
(45) Date of Patent: Apr. 3, 2012

(54) MULTIPOINT AIR SAMPLING SYSTEM HAVING COMMON SENSORS TO PROVIDE BLENDED AIR QUALITY PARAMETER INFORMATION FOR MONITORING AND BUILDING CONTROL

(75) Inventors: Eric M. Desrochers, Millis, MA (US); Gordon P. Sharp, Newton, MA (US)

(73) Assignee: Aircuity, Inc., Newton, MA (US)

( * ) Notice: Subject to any disclaimer, the term of this patent is extended or adjusted under 35 U.S.C. 154(b) by 1147 days.

(21) Appl. No.: 11/373,033

(22) Filed: Mar. 10, 2006

(65) Prior Publication Data
US 2006/0234621 A1 Oct. 19, 2006

Related U.S. Application Data

(60) Provisional application No. 60/660,245, filed on Mar. 10, 2005.

(51) Int. Cl.
*F24F 7/007* (2006.01)
*G01F 17/00* (2006.01)
*G05B 15/00* (2006.01)
*G05B 21/00* (2006.01)
*F25B 49/00* (2006.01)

(52) U.S. Cl. ............. 454/228; 702/50; 700/1; 700/267; 340/632; 62/126

(58) Field of Classification Search .................. 454/228; 702/50; 700/1, 267; 340/632; 62/126
See application file for complete search history.

(56) References Cited

U.S. PATENT DOCUMENTS

| 4,109,615 A | * | 8/1978 | Asano ........................... 123/686 |
| 4,182,180 A | | 1/1980 | Mott |
| 4,205,381 A | * | 5/1980 | Games et al. ................. 700/277 |
| 4,250,381 A | * | 2/1981 | Yoshiike et al. .......... 250/237 G |
| 4,570,448 A | | 2/1986 | Smith |
| 5,246,668 A | | 9/1993 | MacCallum et al. |
| 5,261,596 A | * | 11/1993 | Tachibana et al. ........... 236/49.3 |
| 5,267,897 A | | 12/1993 | Drees |

(Continued)

FOREIGN PATENT DOCUMENTS

JP 05264080 A * 10/1993

OTHER PUBLICATIONS

JP document including Abstract translation.*

(Continued)

*Primary Examiner* — Steven B McAllister
*Assistant Examiner* — Helena Kosanovic
(74) *Attorney, Agent, or Firm* — Brian M. Dingman; Mirick, O'Connell, DeMallie & Lougee, LLP

(57) ABSTRACT

A system for monitoring air quality conditions, comprising, a multi-point air monitoring system comprising, a plurality of sensors for collecting air quality data from a plurality of at least partially enclosed areas; one or more data processing units for processing one or more air quality parameters based on the collected air quality data; and one or more communication devices for communicating the data from the sensor to the processing unit; and a signal processing controller that generates one or more blended air quality parameter signals via the multi-point air monitoring system based at least in part on one or more of the processed air quality parameters representative of data from a plurality of the sensors.

18 Claims, 10 Drawing Sheets

U.S. PATENT DOCUMENTS

| | | | |
|---|---|---|---|
| 5,292,280 | A | 3/1994 | Janu et al. |
| 5,293,771 | A | 3/1994 | Ridenour |
| 5,394,934 | A | 3/1995 | Rein et al. |
| 5,976,010 | A | 11/1999 | Reese et al. |
| 6,125,710 | A | 10/2000 | Sharp |
| 6,241,950 | B1 | 6/2001 | Veelenturf et al. |
| 6,252,689 | B1 | 6/2001 | Sharp |
| 6,369,716 | B1 * | 4/2002 | Abbas et al. ............ 340/632 |
| 6,609,967 | B2 | 8/2003 | Sharp et al. |
| 6,711,470 | B1 | 3/2004 | Hartenstein et al. |
| 6,758,739 | B1 * | 7/2004 | Sangwan et al. ........... 454/75 |
| 6,790,136 | B2 | 9/2004 | Sharp |
| 2002/0144537 | A1 | 10/2002 | Sharp et al. |
| 2006/0060004 | A1 | 3/2006 | Descrochers et al. |
| 2006/0060005 | A1 | 3/2006 | Descrochers et al. |
| 2006/0150644 | A1 * | 7/2006 | Wruck ...................... 62/126 |

OTHER PUBLICATIONS

Warden, David. "Supply Air CO2 Control of Minimum Outside Air for Multiple Space Systems". ASHRAE Journal, Oct. 2004.

Roth, Kurt W., et al. "Demand Control Ventilation". ASHRAE Journal, Jul. 2003.

ASHRAE Standard 90.1 Users Manual.

Ir K.F. Lau and Ir K.W. Chan, Real Time Monitoring with Integrated Control of Air Quality in Buildings, Pub. Sep. 2002, 12 Pgs, Architectural Services Dept, Hong Kong SAR Gov.

Biotest Diagnostics Corporation, "APC Facility Monitoring Software," Publication date at least as early as Jun. 27, 2003, http://www.biotestusa.com/content/view/22/187/.

"Aerospace Building Design Incorporates Concern for IAQ," reprinted from the Indoor Air Quality Update Newsletter, Apr. 1993.

* cited by examiner

MULTIPOINT AIR SAMPLING SYSTEM HAVING COMMON SENSORS TO PROVIDE BLENDED AIR QUALITY PARAMETER INFORMATION FOR MONITORING AND BUILDING CONTROL

CROSS REFERENCE TO RELATED APPLICATION

This invention is a continuation in part of U.S. Provisional Patent Application No. 60/660,245 filed Mar. 10, 2005 titled, "Multipoint Air Sampling System Having Common Sensors Providing Information to Control Aspects of a Building's Environment".

FIELD OF THE INVENTION

This invention relates to air monitoring systems and methods involving the use of multipoint air sampling systems and in some cases discrete local air quality parameter sensors to sense a plurality of air quality parameters to provide blended air quality information and or control signals particularly involving the sensing of humidity and or carbon dioxide. This apparatus and methods can be applied for both monitoring buildings and the control of building functions generally related to regulating an environmental parameter or some aspect of the operation of a building's ventilation system. Specific preferred control embodiments relate at a space or room level to the control of room supply or return air for the dilution ventilation control of spaces or rooms plus the monitoring and control of relative humidity in spaces. At a building or air handling unit level, preferred embodiments relate to the control of the outside airflow into a building for reducing contaminant levels and meeting occupancy based outside airflow requirements as well as the control of outside air using an economizer type approach for operating an air handling unit to enable free cooling with outside air using enthalpy and air contaminant measurements.

BACKGROUND OF THE INVENTION

As is known in the art, there are various means for monitoring indoor environmental or air quality parameters. One approach involves the use of facility monitoring systems or also referred to as multipoint air monitoring systems. In the context of this invention a multipoint air monitoring system is defined as a monitoring system that includes at least one environmental or air quality parameter sensor that measures at least one air quality parameter for a plurality of rooms, spaces, areas, air ducts, or environments within a building or the ambient conditions surrounding or adjacent to a building or facility. As such a multipoint air monitoring system may involve the use of one or more individual, local, wired or wireless sensors located in the space or area being measured. It may also use remote or centralized air quality parameter sensors that are multiplexed or shared amongst a plurality of spaces as is described in more detail later. Finally, a multipoint air monitoring system may use a combination of the previously mentioned remote and local air quality parameter sensors.

Typically, many of these facilities where multipoint air monitoring systems will be employed involve the use of air handling units that involve return air where a percentage of the air returned to the air handling unit is mixed with some percentage of outside air to provide supply air to various rooms or spaces within a building. Alternatively, the building may in some cases contain critical environments such as laboratories or vivariums which are one pass environments that do not use return air and instead exhaust all the air supplied into the critical environment rooms. Although many of the figures of this patent are directed to a building with return air, the invention can also be used for one pass critical environments as well. A related U.S. patent application that involves the use of multipoint air monitoring systems and the blending of air quality parameter sensor signals for dilution ventilation control applications within one-pass critical environments is titled "Dynamic Control Of Dilution Ventilation In One-Pass, Critical Environments" by Sharp and Desrochers and was filed on Mar. 10, 2006 concurrent with this application and is incorporated herein by reference.

For those multipoint air monitoring systems where remote sensors are used, air is transported through a tube or pipe for sampling or measurement purposes. For example, a multipoint air monitoring system may have one or more centrally located air quality parameter sensors instead of distributed sensors local to the sensed environment. As such, this centralized air quality parameter sensor may be used in these systems to sense several or a large number of locations. These centralized air monitoring systems are also referred to in the context of this invention as multipoint air sampling systems, or as multiplexed or shared sensor based facility monitoring systems.

Multipoint air sampling systems are defined for the purposes of this invention as specifically a facility monitoring system that uses shared or multiplexed sensor(s) consisting of either a single remote sensor or a set of remotely located sensors that is used to monitor a plurality of spaces, areas or rooms within a building, or outside adjacent to a facility by transporting samples or packets of air from the spaces to be monitored to the at least one air quality parameter sensor.

For one class of these multipoint air sampling systems specifically defined, in the context of this invention, as star configured multipoint air sampling systems or just star configured systems, multiple tubes may be used to bring air samples from multiple locations to a centralized sensor(s). Centrally located air switches and/or solenoid valves may be used in this approach to sequentially switch the air from these locations through the different tubes to the sensor to measure the air from the multiple remote locations. Each location may be sensed for between 10 seconds or several minutes. Depending on how many locations are sensed each space may be sensed on a periodic basis that could range from 5 to 60 minutes. These star configured systems are sometimes called octopus-like systems or home run systems and may use considerable amounts of tubing.

Systems such as this, for example, have been used to provide monitoring functions for the detection of refrigerant leaks, and other toxic gas monitoring applications. Other systems similar to this, such as that described within U.S. Pat. No. 6,241,950 to Veelenturf et al., which is incorporated herein by reference, discloses a fluid sampling system including a manifold having inputs, common purge and sampling pathways, and valves to couple/decouple first and second sets of inputs for measuring pressure differentials across sample locations.

Additionally, these types of star configured systems have been used to monitor particulates in multiple areas such as clean room areas with a single particle counter. A prior art example of this is a multiplexed particle counter such as the Universal Manifold System and Controller as made by Lighthouse Worldwide Solutions, Inc. coupled with one of their particle counters such as their model number Solair 3100 portable laser based particle counter or an obscuration based particle sensor.

Regarding absolute moisture or dewpoint temperature measurement an example of a prior art star configured multipoint air sampling system that can be used to measure dewpoint temperature is the AIRxpert 7000 Multi-sensor, Multipoint Monitoring system manufactured by AIRxpert Systems of Lexington, Mass., www.airexpert.com.

Another multipoint air sampling system defined in the context of this invention as a networked air sampling system uses a central "backbone" tube with branches extending to various locations forming a bus-configured or tree like approach similar to the configuration of a data network. Air solenoids are typically remotely located proximate to the multiple sampling locations. The sampling time for each location like with the star configured systems may vary from about 10 seconds to as much as several minutes. A typical sampling time per location would be about 30 seconds, so that with 30 locations sampled, each location could be sampled every 15 minutes. Networked air sampling systems can potentially be used to sample locations within a building, an air handling unit ductwork, exhaust air stacks of a building, or outside a building. An exemplary networked air sampling system is described in U.S. Pat. No. 6,125,710 to Sharp, which is incorporated herein by reference. U.S. patent application Ser. No. 09/779,379 to Sharp et. al., titled "Air Quality Monitoring Systems and Methods", references different multipoint air monitoring systems including multipoint air sampling systems as used with expert system analysis capabilities and is also incorporated herein by reference.

Finally another multiplexed form of facility monitoring system that may be used to implement portions of this invention is defined in the context of this invention as a networked photonic sampling system that multiplexes packets of light vs. packets of air and may incorporate either a star configured or network/bus type of layout. The basic concept uses a central laser emitter and a central laser detector that sends out and detects laser light packets that are switched into rooms to be sensed by optical switches. Optical fiber sensors, infrared absorption cells or sensors, and other sensing techniques are located and used in the sensed area to change the properties of the light due to the affect of the environment. The light packet is then switched back to the central detector where the effect of the environment on the light properties is determined. A major benefit of the system is that the sensors such as the fiber or open cell sensors are potentially quite low in cost. The expensive part is the laser and detector systems that are centralized. Similar to the previous multipoint air sampling systems, multiple affects on the light from particles, gases and other contaminants, humidity, etc. can be done simultaneously with central equipment and the telecom concept of Wavelength Division Multiplexing which allows multiple wavelengths and hence multiple signals to share the same fiber. A clear advantage of this system is the ability to have a very rapid cycle time that can be in the ten's of milliseconds or less. This sampling system is detailed in U.S. Pat. No. 6,252,689, entitled "Networked Photonic Distribution System for Sensing Ambient Conditions" and is incorporated herein by reference.

The multipoint air sampling systems and networked photonic sampling system which have been described heretofore and are collectively referred to as sampling systems may be applied to monitor a wide range of locations throughout a building, including any kinds of rooms, hallways, lobbies, interstitial spaces, penthouses, outdoor locations, and any number of locations within ductwork, plenums, and air handlers. To provide control as well as monitoring of these different spaces, virtual sensor signals can be created that in the context of this invention refer to software or firmware variables, or continuous analog or digital signals that can be passed to other systems such as a building control or laboratory airflow control system and are representative of the state of a given space's air quality parameter value. In effect these signals are reflective of what a local sensor would read if it was being used instead of the multipoint air sampling system or networked photonic sampling system otherwise known collectively again as sampling systems.

Multipoint air sampling systems have been used with a wide variety of air quality parameter sensors to monitor a wide variety of air quality attributes or air characteristics of a building or facility. In the context of this invention an air quality parameter sensor is a sensor that can detect one or more air quality attributes or parameters that convert the level of or information about the presence of an air quality parameter into either a continuously varying or else discontinuous pneumatic, electronic, analog or digital signal or else into a software or firmware variable representing the level of or information about the presence of an air quality parameter in a given space. The air quality parameter sensor may be based on any of a variety of sensing technologies known to those skilled in the art such as for example electrochemical, photonic or optical, infrared absorption, photo-acoustic, polymer, variable conductivity, flame ionization, photo-ionization, solid state, mixed metal oxide, ion mobility, surface acoustic wave, or fiber optic. The air quality parameter sensor may be a wired or wireless sensor type and be implemented with various types of physical hardware such as for example micro-electro-mechanical system based (MEMS), nanotechnology based, micro-system based, analog based, or digital based. Additionally, an air quality parameter sensor may sense for more than one air quality parameter, and may include more than one air quality parameter sensor in a single packaged device.

Furthermore, for the purposes of this patent an air quality parameter is defined as an air characteristic that can consist of an air contaminant, an air comfort parameter, or carbon dioxide ($CO_2$). An air contaminant in the context of this patent refers to certain potentially harmful or irritating chemical, biological, or radiological composition elements or properties of the air such as for example CO, particles of various sizes, smoke, aerosols, TVOC's (Total Volatile Organic Compounds), specific VOC's of interest, formaldehyde, NO, NOX, SOX, $SO_2$, hydrogen sulfide, chlorine, nitrous oxide, methane, hydrocarbons, ammonia, refrigerant gases, radon, ozone, radiation, biological and or chemical terrorist agents, other toxic gases, mold, other biologicals, and other contaminants of interest to be sensed. An air contaminant specifically does not refer to such other air quality parameters such as temperature, carbon dioxide, or any one of the many forms of measuring moisture or humidity in air such as for example relative humidity, dewpoint temperature, absolute humidity, wet bulb temperature, enthalpy, etc.

Furthermore, air contaminants can be further subdivided into two categories, gas based contaminants and particle based contaminants. Gas based contaminants are defined in the context of this invention as air contaminants that are gas or vapor based such as CO, TVOC's, ozone, etc. Particle based contaminants on the other hand consist of viable and nonviable air borne particulate matter of any size, but generally of a particle size from 0.01 microns up to 100 microns in diameter. As such this category of contaminants also includes all biological particulate matter such as mold spores, bacteria, viruses, etc.

Carbon dioxide refers specifically to the gas carbon dioxide that is found naturally in the atmosphere as a component constituent in addition to oxygen and nitrogen. It is typically found in outside air at concentrations between 300 and 500 PPM and is exhaled by human beings at an approximate rate of 0.01 CFM per person for a person doing typical office work. Variations in the number of people in an office compared to the amount of outside air supplied into the building can easily vary indoor $CO_2$ levels to between 500 and 2500 PPM. As such $CO_2$ can be used as an excellent indicator of proper ventilation on a per person basis sometimes referred to as the CFM of outside air per person since the level of $CO_2$ in a space is directly related to the number of people in a space divided by the rise in $CO_2$ from outdoor levels. Although high $CO_2$ levels are often associated with poor indoor air quality levels, it is not the level of $CO_2$ itself that creates the discomfort and symptoms associated with poor indoor air quality but instead the associated rise in air contaminants that are not being properly diluted. Human beings are unaffected by relatively high levels of $CO_2$ such as up to 5000 PPM, which would be extremely rare to find in any building of ordinary construction.

For the purposes of this patent an air comfort parameter specifically refers to either the measurement of temperature or one of the many related psychrometric measurements of moisture or humidity in air such as again, relative humidity, dewpoint temperature, absolute humidity, wet bulb temperature, and enthalpy. An air comfort parameter also does not refer to either carbon dioxide or any air contaminants. Additionally, in the context of this invention, an air quality parameter, air contaminant, or air comfort parameter specifically do not include any measure of airflow volume, velocity or pressure such as for example measurements of air volume that may be indicated in units of cubic feet per minute of air or other units, velocity pressure, air speed or velocity, static pressure, differential pressure, or absolute pressure.

In the past, prior art multipoint air sampling systems have been used from time to time to provide monitoring, data logging, alarming, control, or limit functions for one or more individually sensed air quality parameters but not for blended or composite air quality parameter signals.

In the context of this invention, a blended air quality parameter signal, also referred to as a composite air quality parameter signal, is defined as an analog signal, digital signal, optical signal, software or firmware variable or address location or other time based representation of information that is affected by, related to, or in some manner a function of a plurality of air quality parameters relating to one or more locations such as rooms, spaces, areas, air ducts, or critical environments within a building or the ambient conditions surrounding or adjacent to a building or facility. Such a blended or composite air quality parameter signal can be used to realize benefits such as simplicity, accuracy, cost effectiveness, and reliability compared to prior art approaches. The blended signals can also uniquely enable new air flow control applications as described later, as well as be used for general IEQ monitoring, commanding airflow control devices, or used in the control of any aspect of a building's operation to which they are pertinent such in conjunction with its HVAC and building controls system.

Concerning other aspects of the prior art, the alarm or limit function output signals for individual air quality parameters from multipoint air sampling systems have in the past sometimes been communicated to other systems, such as a building management system (BMS) which, based on the state of these functions, can affect aspects of the operation of a building, such as for example the air flow rate to a location within a zone monitored by the multipoint air sampling system in which the monitoring system has detected that an individually sensed air quality parameter has exceeded a predetermined limit. For example, sampling based refrigerant monitoring systems are examples of multipoint air sampling systems that provide alarm/limit functions such as this for individual parameters in which one or more relay contacts or analog output signals (such as 0-10 volt or 4-20 milliamp signals) are provided either locally where the shared sensor or sensors reside or via remote modules that are in communication with the sensor hardware via a digital network. The VASQN8X multipoint refrigerant monitor by the Vulcain division of BW Technologies, is an example of a monitoring system with capabilities such as this. In this way, multipoint air sampling systems have been used to provide a discontinuous signal, typically via a relay contact, which in turn provides a discontinuous control function based on a single air quality parameter. Note that in the context of this patent a discontinuous signal is defined as one with a limited set of values or states such as two or three states and steps between the values with no intermediate values or states. A discontinuous control function in the context of this patent is similarly defined as one with a limited set of output values or states such as two or three and similarly steps between these values with no intermediate values or states.

U.S. Pat. Nos. 5,292,280 and 5,267,897 describe another multipoint air sampling system that monitors a single trace gas, typically carbon dioxide ($CO_2$), at multiple locations, including return air, outside air, and the supply discharge air associated with an air handler in order to directly compute the outside air flow component for purposes of controlling the air handler. This method uses a common $CO_2$ or trace gas sensor and valves assigned to each of the sampled locations to provide a multiplexed signal from the $CO_2$ sensor that varies in time based on the current location being sampled. The time variant signal from the shared $CO_2$ sensor is read by a separate control module, where it is decomposed into three separate $CO_2$ or trace gas signals, based on continuous knowledge of the sequence state, representing outside air, return air, and supply discharge air $CO_2$ concentrations.

A similar multipoint air sampling system prior art method described by Warden in a paper entitled "Supply air $CO_2$ Control of minimum outside air for multiple space systems", David Warden, published in October of 2004 in the ASHRAE Journal applies a common single parameter $CO_2$ sensor, using a three-way valve or two separate two-way valves to alternately switch air samples taken from an air handler's supply discharge air as well as that from outdoors. This creates a multiplexed signal that can be decomposed by a computer in the form potentially of a Direct Digital Control module (or DDC controller) in order to get a reading of supply air $CO_2$ concentration with respect to outside air $CO_2$ concentration that in turn can be used to control the outside air intake to the air handler.

U.S. Pat. Nos. 6,609,967 and 6,790,136 to Sharp and Desrochers discloses methods and apparatus to safely re-circulate air in a controlled ventilated environment for minimizing ventilation and thermal load requirements for each room, and thereby reducing the amount of required outside air. In particular, if one or more individual air contaminants are sensed in one of the rooms of the ventilated environment, the amount of air re-circulated from that room is reduced or potentially shut off to prevent contaminating other rooms in the ventilated environment.

Other prior art systems such as the AIRxpert 7000 Multisensor, Multipoint Monitoring system mentioned above or the networked air sampling system previously mentioned in U.S. Pat. No. 6,125,710 to Sharp discuss measuring multiple individual air quality parameters but again do not discuss how to create or employ a blended air quality parameter signal from these systems.

Additionally, heretofore the use of multiple individual local sensors to create composite signals from multiple locations would have involved a large number of individual sensors used with a building management system (BMS) or data acquisition system with an associated large first cost and large ongoing calibration costs. Multipoint air sampling systems on the other hand can sense multiple parameters cost effectively on a discrete sampled and individual basis, although as mentioned above, means has been lacking heretofore to properly combine and blend this information on a discontinuous or continuous basis so it can be beneficially applied to appropriate monitoring or control applications.

One pertinent application where blended air quality parameter information can be used to significant advantage involves room or area based demand control ventilation (DCV) as applied for example to an office, classroom, assembly, auditorium or variable occupancy space or air handling unit based demand control ventilation as applied to air handler of a building. As described in the previously mentioned paper by Warden entitled "Supply air CO2 Control of minimum outside air for multiple space systems", the outside air into a facility as well as the amount of supply air into a given room or area can be varied based on the amount of people in the facility or the given area or room by measuring a proxy measurement for occupancy and ventilation which is CO2. As described previously, the more people in the space or building the more CO2 rises allowing a measurement of CO2 to drive and increase outside air into the building when the number of people increases or conversely allows the amount of outside air to drop when less people are in the space. Similarly for room or area based demand control ventilation when the CO2 level of an area rises, the supply air into the space can be increased to increase the amount of dilution ventilation in that space and conversely when CO2 levels drop due to a reduction in people in the space such as a conference room, the supply air into the space can be decreased down to the minimum supply air required to handle the room's thermal load to save energy.

Although these two demand control ventilation approaches of room based dilution ventilation control and air handler based outside air control has been used for some number of years, a problem with these concepts is the potential presence of non-human pollutants such as particles, carbon monoxide, TVOC's (Total Volatile Organic Compounds) or other air contaminants that can accumulate and rise in value when a source of them is present and ventilation levels are low. If for example a space is sparsely populated, and some strong and potentially irritating cleaning compounds are used in the space, problems could ensue for those existing occupants since the low level of occupants would have driven the ventilation rates down to a low level when in reality the presence of the cleaning compounds should necessitate a much higher ventilation rate. As mentioned in an ASHRAE Journal article dated July of 2003 titled "Demand Control Ventilation" by authors, Kurt W. Roth, John Dieckmann, and James Brodrick that although "In practice DCV has reduced annual energy costs by $0.05 to $1 per square foot . . . . Currently, most buildings do not use DCV because of concerns about nonhuman indoor pollutants mentioned previously."

In addition to the previously high cost of sensing these non human indoor pollutants or air quality parameters it has also not been known to those skilled in the art of ventilation control how very different air contaminants such as TVOC's, particles, carbon monoxide and others should be used in conjunction with carbon dioxide information, which is itself not a contaminant, to properly control the outside air into the building through blending the elements of both demand control ventilation using CO2 plus dilution ventilation control based on one or more air contaminants.

Referring to another industry problem, although there are many advantages to solely using multipoint air sampling systems as described above to create a composite or blended air quality parameter signal, there are certain air quality attributes that can not be properly detected with the use of at least some if not all of these multipoint air sampling systems. Most notably, temperature can not be sensed remotely with a centralized sensor since the temperature of the air sample pulled through the air sampling conduit or tube will rapidly change temperature to equal the temperature of the sampling conduit or tube. In many cases the air does not need to travel more than 10 to 20 feet before its temperature has been substantially affected by the temperature of the sampling tubing. Furthermore, there are also other air quality attributes such as ozone or particles that depending on the type of tubing used or the speed of transport, may be affected by transport through the tubing.

With respect to temperature, for example, the inability of a remote sensor based multipoint air sampling system to measure the room or duct temperature at air sampling locations creates a problem in measuring such moisture related properties as relative humidity and enthalpy using a multipoint air sampling system. This is because only the absolute humidity, the amount of water vapor in the air in parts per thousand or the dewpoint temperature can be measured directly by a multipoint air sampling system. Thus, the difficulty in obtaining a measurement of the air sample's temperature before it is affected by the air sampling tubing and then combining or blending that temperature measurement with the absolute humidity measurement has in the past prevented the use of these multipoint air sampling systems for the monitoring or control in rooms or in air ducts of the blended air quality parameters of relative humidity and enthalpy.

This is potentially important since local relative humidity and enthalpy sensors, potentially used in the economizer of an air handling unit, are difficult to maintain and keep accurate when used as local sensors particularly for certain applications involving the measurement of outside air due to the wide ranging temperature of this air and it's typically heavy concentration of particulates and dust. For example, a recent study by the New Buildings Institute of economizers and air handling units in the Pacific Northwest stated that approximately two thirds of the economizers evaluated were not working properly or had failed completely in many cases due to the failure of the sensors.

To explain this application in more detail, an economizer as defined in the context of this patent is a system that exists as a part of a building air handling system for reducing cooling costs by introducing outside air in lieu of, or to assist with, mechanical cooling such as mechanical equipment based air conditioning. The effectiveness of an economizer is largely based on its ability to sense when outside air conditions are suitable so that the outside air can be used for so-called "free cooling" to reduce compressor use. U.S. Pat. Nos. 4,182,180 and 4,570,448, which are incorporated herein by reference, disclose exemplary techniques for using outside air for cooling. This includes dry-bulb temperature, single enthalpy, and differential enthalpy based economizers. Of these types of economizers, enthalpy based types (particularly differential enthalpy based economizers) have demonstrated better performance, especially in hotter more humid climates, where the latent heat load associated with cooling outside air can be a significant factor. For this application, enthalpy sensors are available for use with economizers such as Honeywell Part No. C7650, solid state economizer control.

Although the savings potential with enthalpy based economizers can be significant, these systems as mentioned above, often realize limited savings in practice due in part to issues with unreliable sensor technology, as is well known in the art. ASHRAE (American Society of Heating, Refrigerating and Air-Conditioning Engineers) has commented on the limited reliability of these sensors such as in the ASHRAE Standard 90.1 Users Manual. Known enthalpy sensors were based on a plastic filament that could deteriorate over time leading to failure or gross calibration errors. Newer sensors are based on solid-state designs, but they are still subject to drift and repeatability problems.

Centralized remote absolute humidity and chilled minor hygrometers are much more accurate, reliable and cost effective when used as part of a multipoint air sampling system. If the aspect of local temperature measurement could be cost effectively solved then these sensors could be advantageously used for the more commonly used measurements of relative humidity and enthalpy.

Another problem with economizers is that there are times when outdoor conditions are worse than indoor conditions such as with a building located near a major highway during rush hours. During these periods if the economizer is calling for free cooling, potentially 100% outside air is being drawn into the building which may be saving energy, but due to the high traffic outside the building the indoor air quality of the facility may actually be made worse. As a result it would be helpful to be able to create a blended outdoor air contaminants signal incorporating multiple air contaminants such as TVOC's, CO, and potentially particles that could be used with the air handler to override the economizer's control of outside air when the outside air is "dirty".

One known problem with dilution ventilation in buildings using air contaminant sensors such as for example sensors for particles, CO, TVOC's or other air contaminants is that if the outside air concentrations becomes high enough, increasing the airflow volume of outside air or the supply air into a controlled area or room will actually increase the sensed air contaminant levels in a space, duct or air handler. This can potentially create a negative feedback situation when the inside dilution ventilation threshold levels are exceeded forcing the outside airflow levels and or room supply air flow levels to their maximum level. Depending on the level of design capacity of the HVAC system, the capacity of the air handling system could be exceeded in this latch-up situation, causing a degradation of HVAC system control.

SUMMARY OF THE INVENTION

It is therefore a primary object of this invention to provide a system for providing blended air quality parameter measurements derived from individual air quality parameter measurements using at least in part a multipoint air sampling system and in some cases also local discrete air quality parameter sensors.

It is a further object of this invention to provide a system for providing air quality parameter measurements of improved accuracy and cost effectiveness that cannot be achievable with the use of either only discrete local sensors or the use of only a multipoint air sampling system.

It is also an object of this invention to provide systems and methods for providing cost effective and accurate blended air quality parameter sensor measurements of a type not available commonly in the past for the purposes of controlling building HVAC (Heating, Ventilating, and Air Conditioning) operations and equipment including controls equipment.

It is another object of this invention is to enable specific control and monitoring applications involving the creation of blended air quality parameter measurements of relative humidity and or enthalpy that can be done more cost effectively and accurately with the use of the invention.

It is also an object of this invention to enable an improved and more healthy form of demand control ventilation involving the creation and use of an improved outside air control signal and or a supply airflow control signal. These control signals are also known as outside air command signals and or dilution ventilation command signals. They can for example be created using a blended air quality parameter signal that may typically incorporate aspects of carbon dioxide level information to implement aspects of demand control ventilation; as well as information from at least one other air quality parameter measurement such as TVOC's, particles, carbon monoxide, or even humidity to assist in maintaining good air quality in a space or a building by providing adequate levels of supply airflow to a space and or outside airflow into a building to dilute any such sensed air contaminants down to safe or recommended levels.

The latter embodiment of the current invention is implemented using the virtual signals from a multipoint air sampling system and or the signals from local room or duct air quality parameter sensors and combines them via one or more of multiple approaches using a signal processing controller or other means such as a building control system to create a dilution ventilation command signal and or an outside airflow command signal. In the context of this invention a dilution ventilation command signal is defined as an airflow command signal that can be used to vary, at least partially the supply airflow rate into a monitored room or space based on sensed air quality parameter information. The purpose of this control signal is to appropriately increase ventilation when air contaminant levels in a space or building are too high, typically to improve indoor air quality, and to decrease airflow levels, typically to save energy, when both the number of occupants in a space is reduced and the air is relatively clean of contaminants.

In the context of this invention an outside airflow command signal is defined as an airflow command signal that can be used to vary, at least partially the outside airflow into a building or air handling unit based on potentially multiple factors. These factors include for example the sensed air quality parameter information inside the building, the sensed air quality parameter information outside the building, the comparative levels of inside and outside sensed air quality parameters, the amount of free cooling to optimize energy efficiency and comfort, and the amount of outside airflow required to meet recommended guidelines based on the real time or design occupancy of for example the entire area of the building served by a particular air handling unit, specific critical areas served by the air handling unit, or areas served by the air handling unit with varying occupancy. The purpose of this control signal is to balance energy savings from free cooling and demand control ventilation with providing enhanced indoor air quality through increased dilution of internal contaminants and preventing the excessive use of outside air when it is "dirty" or has excessive levels of air contaminants.

For the purposes of this patent, an airflow command signal is any pneumatic, electronic, analog or digital signal, or a software of firmware variable that operates in a firmware or software program running on a microprocessor or computer; and that is used by the room airflow controller, the outside airflow controller, the building control system, by one of the return, exhaust, or supply airflow control devices located in a room or space within the building, or by an outside airflow, recirculated airflow, or building exhaust airflow control device or damper often associated with a building's air handling unit or HVAC system. These command signals serve to at least partially vary or control one or more of the aspects of or relationships between any one of the airflows moving into or exiting the building, an air handler or an area, space, room or environment within the building. If the airflow command signal is of a continuously varying nature it can be referred to herein as a VAV or variable air volume command signal. Otherwise, the airflow command signal may be a discontinuous airflow command signal which in the context of this invention is defined as a signal that may have only two levels or states and for the purposes of this patent is referred to as a two state signal, or it may have three levels or states and may thus be referred to in the context of this invention as a three state signal. Alternatively, the discontinuous airflow command signal may have multiple discrete levels or states and as thus may be referred to herein as a multiple state signal.

For the purposes of this invention a signal processing controller as mentioned above refers to analog or digital electronic circuitry, and or a microprocessor or computer running a software or firmware program that uses at least information, signals and or software or firmware variables from either individual local sensors of air quality parameters plus virtual sensor signals, information and or software or firmware variables from remote or centralized sensors of air quality parameters, and blends, combines or processes this information in a potential multitude of ways. As a result the signal processing controller either creates airflow command signals for building outside airflow control, for dilution ventilation, offset air volumes, or other airflow commands to be used by a room airflow controller, and or for creating signals or information that can be used by other control devices such as a building control system for at least partially controlling building level airflows including outside airflow into the building as well as one or more room airflows of supply, return, exhaust or offset airflow, and or is used for some other control or monitoring function that is in some way related to the control of one of the aforementioned room or building airflows.

In the context of this invention, a building control system or building management system as mentioned above is defined as a control system located in a building or facility that is used to control one or more functions of the HVAC system in a building such as for example control of space temperature, space relative humidity, air handling unit airflows and operation, exhaust fan flows, chiller operation, economizer operation, duct static pressures, building pressurization, and critical environment airflows. These systems often integrate with or incorporate other building systems or subsystems such as fire and security, card access, closed circuit TV monitoring, smoke control systems, power monitoring, tracking airflow control systems, and critical environment airflow control systems. Building control systems may have pneumatic, electric, electronic, microprocessor, computer, or web based controls using pneumatic, analog and or digital signal inputs and outputs. These systems often have centralized monitoring functions, centralized or local control capabilities, and may have Internet or web based access. They may also be referred to as building management systems (BMS), facility control systems (FCS), or facility management systems (FMS).

It is another object of this invention to provide systems and methods for preventing dilution ventilation and outside airflow control from becoming latched up at high flow rates due to high outdoor levels of air contaminants. A preferred embodiment to solve this issue for outdoor air control involves using blended air contaminant signals for control that are created from taking the differential of indoor to outdoor contaminant levels vs. the absolute indoor levels. The use of a multipoint air sampling system provides uniquely high accuracy to make this application possible since both indoor and outdoor measurements are made with the same sensor substantially reducing normal sensor errors that would typically be magnified when taking the difference between two different sensors. Likewise a preferred embodiment to solve this issue for room based dilution ventilation control involves using blended air contaminant signals for control that are created using a shared sensor air sampling system that generates a differential air contaminants signal using the difference between the measurements of area or space contaminant levels compared to the levels of contaminants in the supply air feeding the monitored area or space.

Lastly, when multiple air quality parameters are to be used by a signal processing controller to help create a dilution ventilation or outside airflow command signal, particularly where each air quality parameter has a different threshold of concern, each air quality parameter can be scaled to a standard scale relative to that threshold. For example 2 volts in a 0 to 10 volt scale can represent the threshold at which point the airflow should begin to be increased with 10 volts representing maximum flow. The individual signals can then be either high selected so the higher of these signals controls the dilution flow. Alternatively, the signals can be summed together after they have been weighted in a relative manner based on the severity of the health effects of each sensed compound or the previous threshold based weighting. Non linear weighting may also be used where for example the increased level of a dangerous contaminant over a threshold calls for much higher airflows such as for carbon monoxide versus a more benign but still important contaminant such as particles.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

Figure 1:
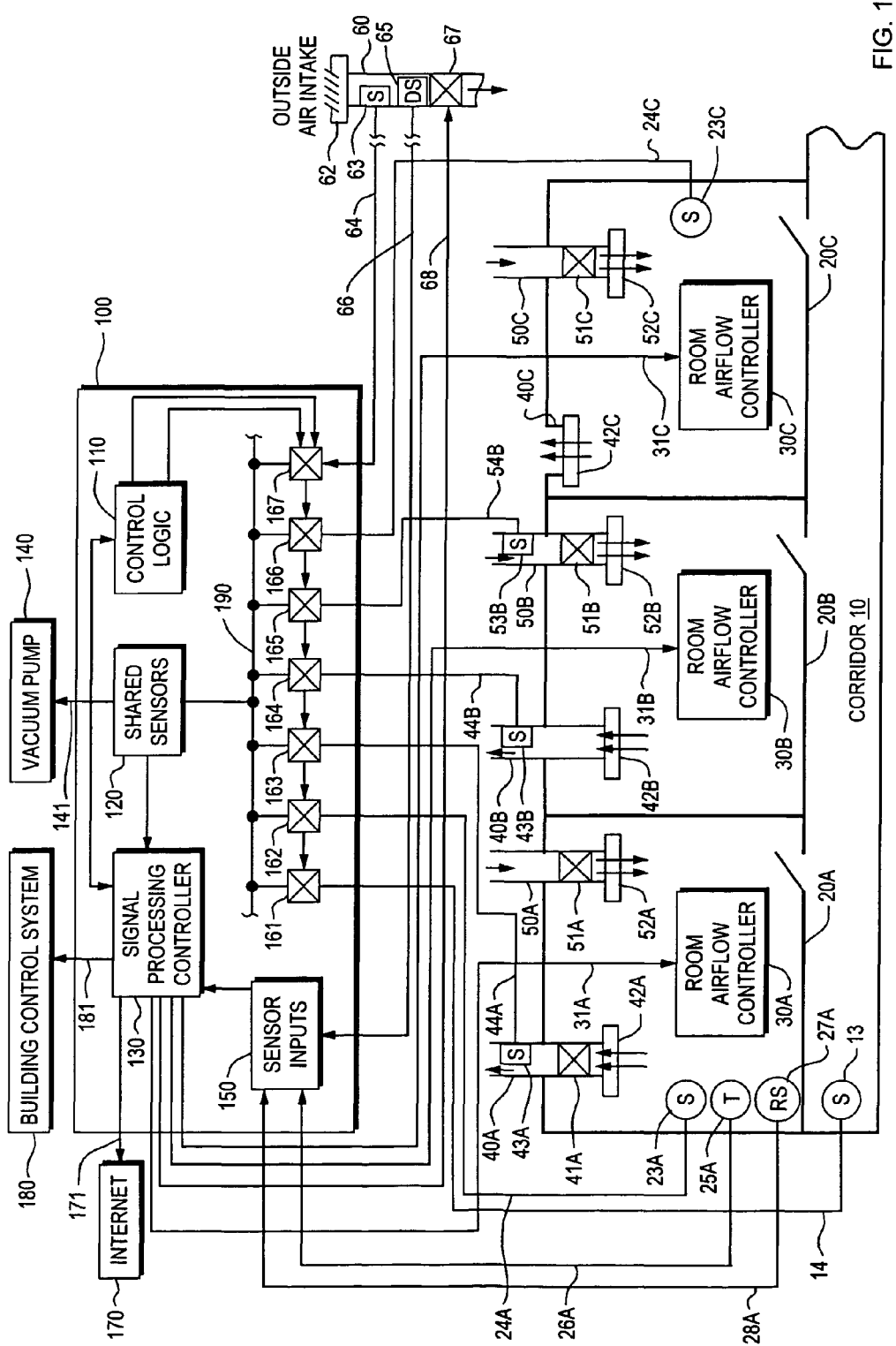
FIG. 1 is a schematic diagram of a preferred embodiment of the system of the invention in which a plurality of spaces and air ducts are being monitored by a multipoint star configured air sampling system.
Figure 2:
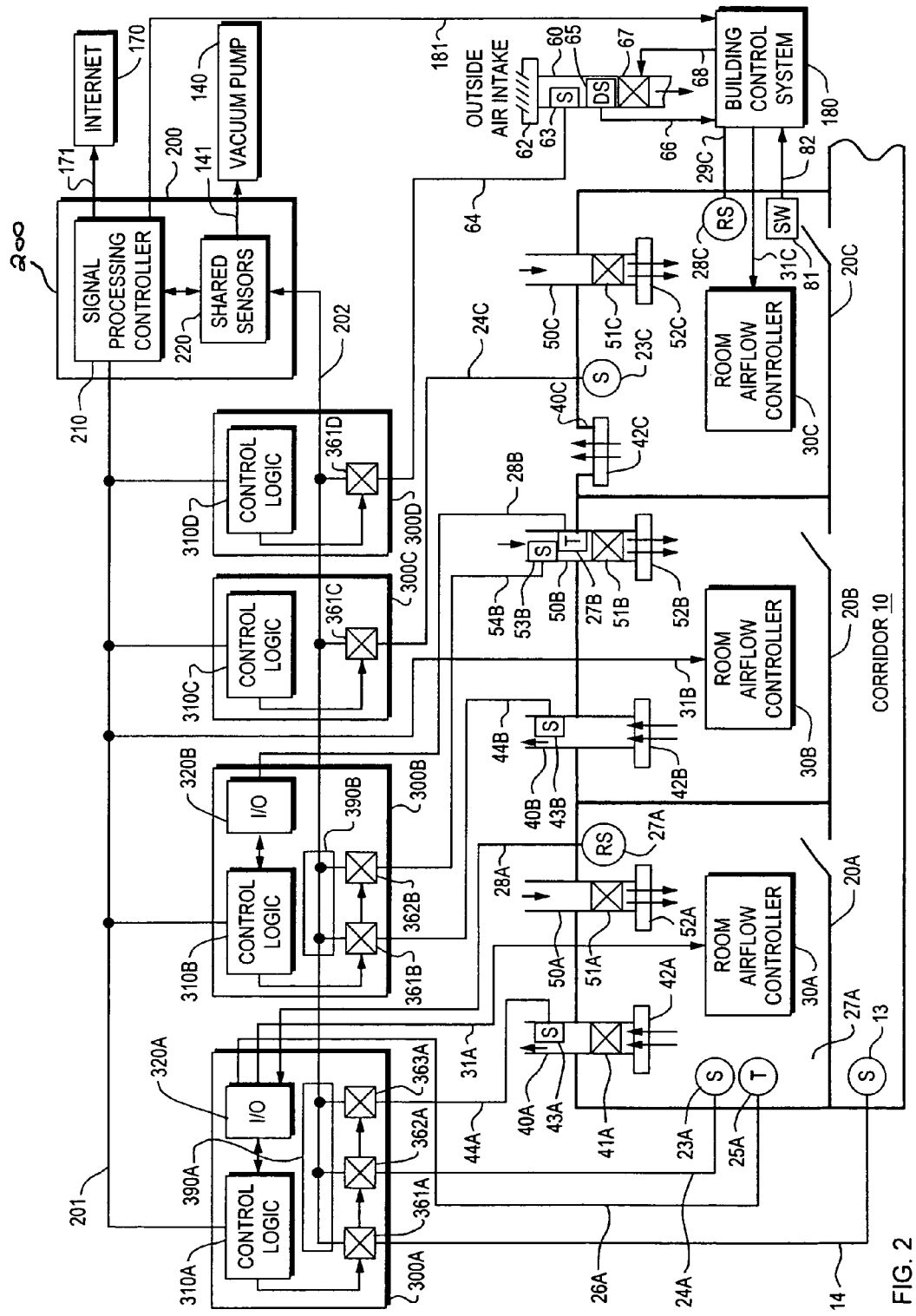
FIG. 2 is a schematic diagram of a preferred embodiment of the system of the invention in which a plurality of spaces and air ducts are being monitored by a multipoint networked air sampling system.

FIGS. 1 and 2 show a typical set of monitored environments or rooms 20A, 20B, and 20C that have doors entering a corridor 10 that is also being monitored. Although the diagrams show three rooms and a corridor, the present invention may be used with just one room or space or monitored area or any plurality of rooms or spaces including corridors or other adjacent spaces that are also being monitored, such as for example, two or more rooms, or one corridor plus one or more spaces. Note also that, although the environments shown in the Figures are enclosed within walls, monitored environments, spaces or areas in the context of this invention may also be a section or area of a room having no walls or partitions around it. Thus, there may be multiple monitored environments within one physical room. Alternatively, multiple physical rooms may also constitute one environment or space. Typically, the environment 20 will also be an area that is fed by one or more supply airflow control devices 51. Potentially a return airflow device 41A may be used that is controlled by room airflow controller 30 or there may be no controlled return air flow devices such as in rooms 20B and C. In the latter two cases the supply air may make its way back to the air handler via transfer ducts 40B or ceiling grill 42C into a plenum space that is typically in a ceiling space that eventually connects to the return airflow inlet of an air handling unit such as air handler unit 1000 in FIG. 6 that is providing the supply air into or near the space. For the purposes of this invention a room airflow controller such as room airflow controller 30 is an airflow control apparatus that may be of analog or digital electronic design or may be constructed using a microprocessor or computer running a software or firmware program that creates the airflow command signals for one or more supply and or return airflow control devices possibly using information, signals and airflow commands from other devices, systems or controllers.

Figure 6:
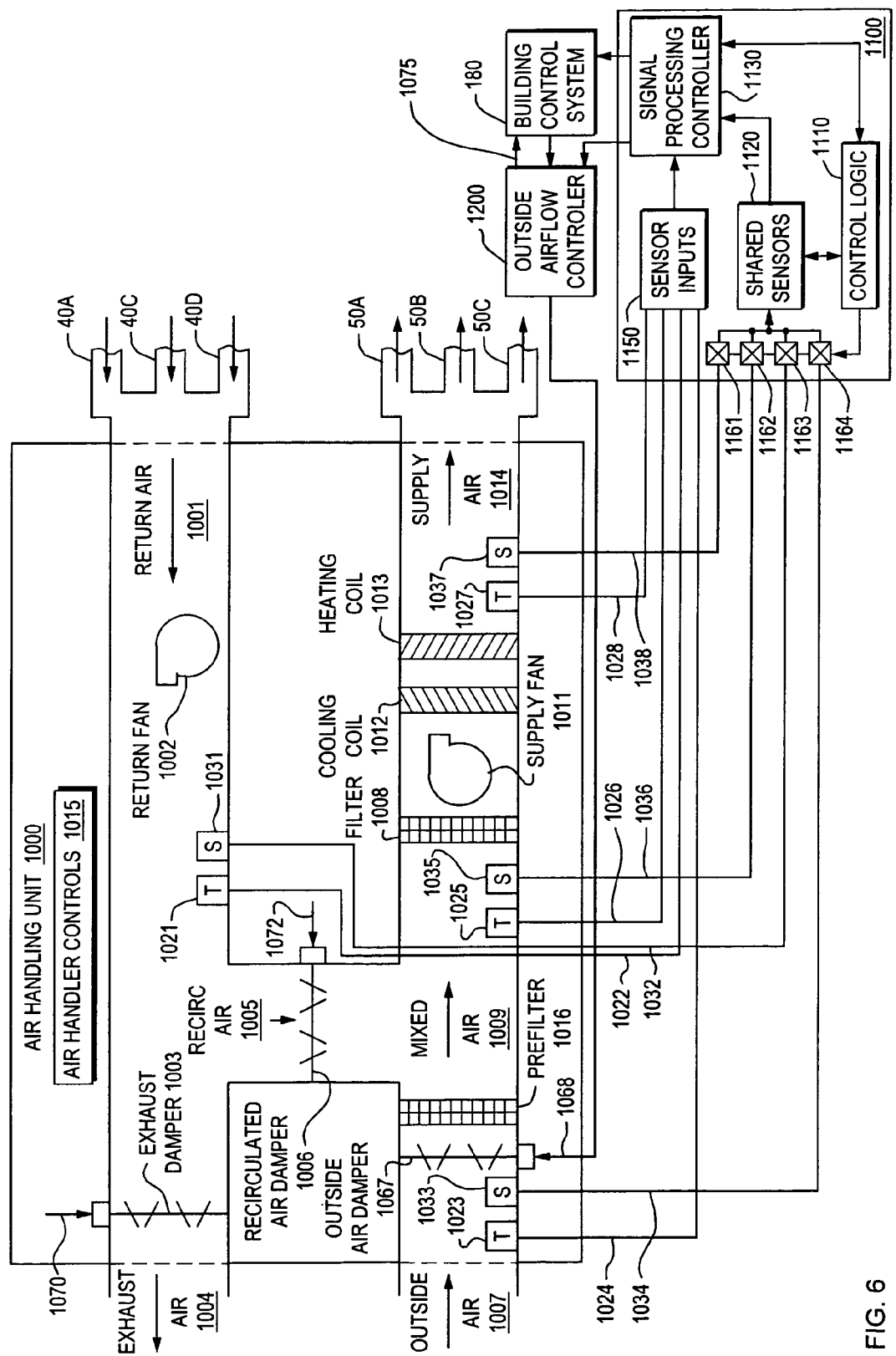
FIG. 6 is a schematic diagram of a preferred embodiment of the system of the invention in which a building air handling unit incorporating return air is being monitored by a multipoint air sampling system.

These sets of rooms in FIGS. 1 and 2 are further described as having a source of supply air from supply air ducts 50A, 50B, and 50C, originating from air handler unit 1000 in FIG. 6, that may exit the room as return air through a plenum space or from controlled return duct 40 A, uncontrolled return duct 40B, or plenum space 40C. Although not shown in the figures, the corridor 10 often has a source of supply air as well. The supply ducts 50A, B and C also contain airflow control devices 51A, B, and C. which supply air into the room or space through supply flow grill or diffuser 52A, B, and C respectively. Additionally, the room return duct 40A contains return airflow control devices 41A which controls the amount of room or space air pulled into the return duct. Return duct 40A, return transfer duct 40B, and plenum space 40C connect to the rooms 20A, B, and C through a room return grill or vent opening 42A, B, and C respectively.

FIGS. 1 and 2 also show the presence of an outside air intake 62 into the building through outside air duct 60. This duct could be connected to or part of some type of an air handling unit, such as the air handling unit 1000 in FIG. 6, to pull in outside air into the building, it may be a source of dedicated outside or make up air into the building not associated with air handler unit 1000, or it may be an outside air pickup location specifically used for or shared by the air sampling systems 100 and 200 of FIGS. 1 and 2 respectively. An outside airflow control device 67 is also shown as a means to vary and control the amount of outside air entering the building.

An airflow control device as used in the context of this invention, such as supply, return, and outside airflow control devices 51A, 41A, and 67 respectively are defined as any device known to those skilled in the art of airflow control for controlling air flow volume and velocity through a duct or opening. For example, they can be constant volume, two state, multiple state, or variable air volume (VAV) boxes or terminals such as manufactured by Titus, Metal Aire, Enviro-Tec, or others. These devices use a damper or throttling device of some type such as a single round, square, or rectangular blade damper, a multiple blade damper, a set of pneumatic bladders that can be used to seal off an opening, or any other type of throttling device that can be used to seal off a duct, that is connected to a pneumatic, electric, or electronic actuator that is controlled by a pneumatic, electronic, digital, or microprocessor based controller which typically also relies on feedback of flow from a flow sensor for closed loop control of the duct's air volume. These flow sensors can be of various types known to those skilled in the art, such as those based on single or multiple velocity pressure sensors, hot wire, heated thermistor, microelectronic flow sensor, etc.

Alternatively, another type of flow control device that is commonly used is an airflow control valve that typically has a venturi shaped body with a spring loaded cone that moves through the venturi shaped throat of the device to provide inherent, pressure independent control of volume, such as manufactured by Phoenix Controls or others. These valves typically have pneumatic, electric, or electronic actuation to provide constant volume, two-state, multiple state, or variable air volume control. These devices often have large turndown or flow ranges that make them very appropriate for control of dilution ventilation that can have wide flow ranges to achieve optimum energy savings and safety.

Finally, another example of an airflow control device may simply be some form of a single or multiple blade damper or other type of throttling device that is located either in an air handling unit, such as the dampers 1003, 1006, and 1067 in air handling unit 1000 in FIG. 6, an outside air duct, or a duct serving one or more areas. These throttling or damper devices may or may not further be used with one of the airflow measuring devices aforementioned or similar airflow measuring devices that are adapted using a grid of sensors or sensing holes for example to measure the airflow accurately across a large cross sectional duct area. As an example, outside airflow dampers providing airflow into an air handling unit are often not used in conjunction with an airflow measuring device. Alternatively, other indirect means of sensing the outside airflow may be used to provide better control of the outside airflow control device.

With reference to FIG. 1, this diagram refers to a preferred embodiment of the present invention directed to control of rooms or areas using blended air quality parameter signals from a star configured multipoint air sampling system 100. Multipoint air sampling system 100 could be a star configured multipoint air sampling system with a structure like that described in U.S. Pat. No. 6,241,950; U.S. Pat. No. 5,292,280; U.S. Pat. No. 5,293,771 or U.S. Pat. No. 5,246,668. It could also be a refrigerant and toxic gas monitor adapted for this purpose such as the Vulcain Inc. multipoint sample draw gas monitor model number VASQN8X as can be seen on their website at www.vulcaininc.com or a multiplexed particle counter such as the Universal Manifold System and Controller made by Lighthouse Worldwide Solutions, Inc., as can be seen at their website at www.golighthouse.com, coupled with one of their particle counters such as their model number Solair 3100 portable laser based particle counter or an obscuration based particle sensor. It could also be a star configured multipoint air sampling system like that of the AIRxpert 7000 Multi-sensor, Multipoint Monitoring system manufactured by AIRxpert Systems of Lexington, Mass., as can be seen at their website at www.airexpert.com.

In FIG. 1, a set of solenoid valves 161 through 167 is part of a multipoint air sampling system 100. Equivalently, these solenoids 161 through 167 could be replaced with other switching means such as SSS-48C Single Scanivalve System manufactured by the Scanivalve Corporation of Liberty Lake, Wash. as can be seen on their website, www.scanivalve.com, which uses a pneumatic selector switch and stepper motor to connect one of many input ports to an outlet port which can be connected to a sensor such as a pressure sensor. The solenoid valves 161 through 167 are controlled to switch in a sequence by control logic 110. This sequence may be a simple sequential pattern of one solenoid after another, or varied for example through programming to be one of potentially many preset patterns, or it can have a pattern that can be interrupted and changed to a new sequence by manual or remote command or by a trigger event based on the values or signal pattern of one or multiple sensed air quality parameters. This trigger event could be generated from outside the multipoint air sampling system 100 or could be created from the sensor information processed by signal processing controller block 130.

The solenoid valves 161 through 167 are connected to sampling locations 13, 23A, and 23C in the spaces as well as duct sensing locations 43A, 43B, 53B, and 63 through tubing 14, 24A, 44A, 44B, 54B, 24C, and 64. In FIG. 1 for example, sampling location 13 in corridor 10 is connected through tubing 14 to solenoid 161. Area sensing locations 23A and C in rooms 20A and C are connected through tubing 24A and C to solenoids 162 and 166 respectively. Return duct sampling location 43A and return transfer duct sampling location 43B are connected through tubing 44A and B to solenoids 163 and 164 respectively. Supply duct sampling location 53B is connected through tubing 54B to solenoid 165. Finally outside air duct sampling location 63 is connected through tubing 64 to solenoid 167. Alternatively, tubing 64 may be connected to some other suitable location other than duct 60 to obtain outside air samples.

The tubing mentioned above transports the air sample from the sensing location to the solenoid of the multipoint air sampling system 100. The tubing typically will have an inner diameter of one eighth to one half an inch in diameter with a preferred inner diameter of about one quarter inches. This tubing can be made of standard plastic pneumatic tubing such as Dekoron™ low density polyethylene (LDPE) plastic, Teflon, stainless steel, "Bev-A-Line XX" tubing made by Thermoplastic Processes, Inc. of Stirling, N.J., or other suitable tubing materials known to those skilled in the art. For superior performance in transporting both TVOC's and particles however, a material that is both inert to VOC's with very little adsorption and desorption as well as electrically conductive to prevent static buildup is preferred such as flexible stainless steel tubing. Other preferred materials and constructions are described in U.S. patent application Ser. No. 10/948,767, filed on Sep. 23, 2004 entitled, "TUBING FOR TRANSPORTING AIR SAMPLES IN AN AIR MONITORING SYSTEM", as well as U.S. patent application Ser. No. 11/149,941 filed on Jun. 10, 2005, entitled, "AIR MONITORING SYSTEM HAVING TUBING WITH AN ELECTRICALLY CONDUCTIVE INNER SURFACE FOR TRANSPORTING AIR SAMPLES".

Additionally in FIG. 1, a vacuum pump 140 pulls air from the sensing locations through the tubing into the solenoids 161 through 167 and into a manifold 190 connecting all the output ports of the solenoids together and to the inlet of the shared sensors 120. The outlet of the shared sensors 120 is connected to the vacuum pump by tubing 141, whose construction is not critical and can be inexpensive plastic tubing such as the Dekoron™ mentioned above or other. The inner diameter of this tubing can be made similar to the size of the tubing connecting to the inlets of the solenoid valves or possibly larger for less pressure drop. The shared sensors 120 can consist of one or more sensors to measure such air comfort parameters as absolute humidity or dewpoint temperature, carbon dioxide, non-air quality parameters such as differential static pressure, or air contaminants such as for example, CO, particles, smoke, TVOC's, specific VOC's of interest, formaldehyde, NO, NOX, SOX, nitrous oxide, ammonia, refrigerant gases, radon, ozone, biological and or chemical terrorist agents, mold, other biologicals, and other air contaminants of interest to be sensed. These sensors may be connected in series, in parallel or a combination of both.

The signal outputs of the shared sensors 120 are passed to the signal processing controller block 130 of the multipoint air sampling system 100. This block 130 also takes in other sensor information from the sensor inputs block 150. This input block 150 accepts sensor signals or information from local room or duct sensors if needed or desired rather than remote sensors. For example, temperature cannot be sensed remotely, since the temperature of the air will change rapidly to the temperature of the tubing as it moves through the tubing. Additionally, some areas may need instantaneous sensing of an air quality parameter. This is shown in Room 20A where room sensor 25A, which could for example be a temperature sensor, is connected to the sensor inputs block 150 through electrical cable 26A. If a temperature sensor is used for 25A and is located near the sampling inlet 23A, then a shared sensor absolute humidity or dewpoint temperature measurement of that location can be combined or blended with the temperature measurement from sensor 25A to create a very accurate and cost effective measurement of relative humidity, enthalpy or one of the other related psychrometric measurements. Likewise if outside air duct sensor 65 is used to measure temperature then the combination of a shared sensor absolute humidity measurement or dewpoint temperature measurement from sampling location 63 which may be located close to sensor location 65 will allow the calculation of an outside air measurement of relative humidity, or enthalpy.

The sensors and the sensor inputs block may operate with many signal forms such as analog voltage, analog current, or digital. Alternatively, the sensor may have its own onboard microprocessor and communicate with the sensor inputs block 150 through a data communications protocol such as, for example, LonTalk by Echelon Corporation, or an appropriate protocol outlined by ASHRAE's BACnet communications standards, or virtually any other appropriate protocol, including various proprietary protocols and other industry standard protocols commonly used to provide data communications between devices within a building environment. Typically, however, when digital data communications are used to connect to discrete devices such as 25A, this is accomplished using a protocol operating over a physical layer such as an EIA485 physical layer, on top of which a suitable upper level protocol will be used. In such cases, for example, cable 26A may be specified as a twisted shielded conductor pair. Nevertheless the connections between sensor 25A and input block 150 may be accomplished using any number of cable types common to the building controls industry. Additionally, cable 26A may be omitted and the sensor 25A may communicate wirelessly to inputs block 150 using such protocols and approaches as IEEE 802.11a/b/g, Zigbee, Bluetooth, mesh networking or other wireless methods used in the building and IT (Information Technology) industry.

The signal processing controller block 130 is used to process the sensor information from the shared sensors to create virtual sensor signals reflective of the environmental conditions in the sensed locations. This information is added to the information from any local room sensors such as 25A or duct sensor 65, and may be further processed to create blended or composite air quality parameter signals and is then used in a variety of possible ways. For example, this information can be sent to building control system 180 for monitoring and or control purposes through a digital networked connection 181. The information interchange could be done using for example, a BACnet protocol, Lonworks, OPC, XML data interchange or other suitable interface information conversion. The physical connection 181 could be an Ethernet connection, EIA485 (also known as RS485) connection or other type of digital data communications connection. Another use of the data can be to send it through an internal and or external local area or wide area network for monitoring at a remote location. Additionally, the data can pass directly, or through a local area network, phone network or other suitable connecting means 171 to connect to the Internet or a dedicated network from which a website or other suitable means can be used to remotely access, display, and analyze the data from the multipoint air sampling system 100.

Most importantly, signal processing controller block 130 can also provide the control signals 31 used by the room airflow controller 30 which in FIG. 1 is shown as blocks 30A, B, and C and dilution ventilation command signals 31A, B, and C. Control signal 31 is used to dynamically vary the minimum supply airflow rate of the spaces which also equivalently controls the amount of dilution ventilation for rooms 20A, 20B, and 20C. Since one of the air quality parameters that can be sensed by the shared sensors is carbon dioxide, a blended dilution ventilation command signal can also include information relating to carbon dioxide levels in a given space to implement a local room level demand control ventilation approach that responds to varying occupancy. Also, given the flexible nature of the electronics associated with room airflow controller 30, part or all of the functions performed by signal processing controller 130 may be performed within room airflow controller 30, which can be a programmable device. In this case, signal 31 may at least in part be created within controller 30.

Referring to dilution ventilation command signals 31A, B, and C, the signal processing controller block 130 can produce these signals, portions of the signals, or all or a portion of the control functions can be produced by the building control system 180. This is shown for example in FIG. 2 with dilution ventilation command signal 31C using sensor information, particularly air quality parameter sensor information from the shared sensors 220 in FIG. 2, and or the local room sensors such as 28C. Further, it should be clear that signal processing controller 130 of FIG. 1, signal processing controller 210 of FIG. 2, or signal processing controller 1130 of FIG. 6 need not be physically packaged within blocks 100, 200, or 1100 respectively and that it's possible to implement signal processing controllers 130, 210, or 1130 as either standalone modules, or to integrate them with some other portion or system shown for example within FIG. 1, 2, or 6.

With reference to FIG. 2, this diagram refers to another preferred embodiment of the present invention directed to creating blended or composite air quality parameter measurements and dilution ventilation airflow command signals using a networked air sampling system such as one similar to that described in U.S. Pat. No. 6,125,710. This sampling system has many of the functions and is similar to the system indicated in FIG. 1 with the main difference being that the solenoid switches and some of the controls are distributed throughout the building vs. being located in one central unit. As a result, central sampling unit 100 shown in FIG. 1 is effectively replaced by sensor and control unit 200, along with distributed air and data routers 300A, 300B, 300C, and 300D. The control of the sequencing of the system and the signal processing functions are handled by signal processing controller block 210. This block 210 carries out the functions of blocks 510 and 530 in FIG. 4, which will be described later. The shared sensor block 220 carries out the same function as block 520 of FIG. 4 or block 120 of FIG. 1.

Blocks 300A, B, C and D are air and data routers that house the solenoid valves 361A, 362A, 363A, 361B, 362B, 361C and 361D as well as potentially some analog or digital input and output capabilities that are contained in Input/Output blocks 320A and 320B. As an example, air sampling location 23A is connected via tubing or air transport conduit 24A to solenoid 362A that is part of air and data router 300A. This tubing or air transport media 24A along with 44A, 14, 44B, 54B, 24C and 64 was described earlier except that the air transport conduit may also have associated with it some additional electrical conductors for the purpose of adding networked data communication, low voltage power, signal wires and other potential functions as described in U.S. patent application Ser. No. 10/948,767, filed on Sep. 23, 2004 entitled, "TUBING FOR TRANSPORTING AIR SAMPLES IN AN AIR MONITORING SYSTEM", as well as U.S. patent application Ser. No. 11/149,941 filed on Jun. 10, 2005, entitled, "AIR MONITORING SYSTEM HAVING TUBING WITH AN ELECTRICALLY CONDUCTIVE INNER SURFACE FOR TRANSPORTING AIR SAMPLES" both hereby incorporated herein by reference. Adding these conductors enables local sensors to be more conveniently and cost effectively added to the system.

For example, sampling location 23A, as well as the other sampling locations 43A, 43B, 53B, 24C and 63, could also contain a local temperature sensor similar to that of local sensor 25A integrated into the sampling location to sense the room or duct temperature. The signal from this temperature sensor or from other local sensors such as humidity, ozone, or other local air quality parameter characteristics can be sent to the air data router 300 as a digital data communications signal though a data communication cable such as a twisted pair, twisted shielded pair, fiber optic cable or other digital data communications media. Alternatively, the sensor information could be sent to the router 300 via an analog signal through one or more signal conductors as an analog voltage or current signal. This analog signal can then be converted to a digital signal by the I/O block 320A or 320B in the router 300A or 300B respectively.

These I/O blocks 320A and 320B can also monitor other air quality parameters or signal inputs that may or may not be directly associated with an air-sampling inlet yet would have a data communications cable, analog signal cable, or other connection to the I/O block. An example of one of these sensors is room sensor 27A which could be a temperature sensor, an air quality parameter sensor or other type of sensor such as a light, differential pressure, air velocity or other building sensor such as an occupancy sensor or occupancy switch, or even another type of switch of some type such as local room switch 81. Of the latter sensors or room switches, an occupancy sensor is defined in the context of this invention as a sensor that can detect the presence of people in a space through infra red energy, motion, card access, or other means, whereas an occupancy switch is defined in the context of this invention as a room switch such as a manually operated light switch or other type of room switch operated by the occupant when they enter or leave the space. A room switch in the context of this invention is defined as some type of switch that may be for example electrical, mechanical, photonic, or pneumatic that is located in or near the environment that can be manually operated to signal a change in state to a system connected to it. A room switch may for convenience of sharing wiring be located in the same room location and possibly in the same enclosure as the air sampling pickup. Other types of room switches or sensors could also be connected to the I/O blocks 320 of the air and data routers 300.

Within the air data routers 300, the output of multiple solenoid valves can be manifolded together with manifold 390A and B. These manifolds plus the outputs of individual solenoid valves such as 361C in air and data router 300C or solenoid 361D in router 300D are connected together with tubing or air transport conduit 202 to transport air samples to shared sensors 220 in the multipoint air sampling unit 200 as moved by vacuum source 140. The control of the air and data routers as well as the communication of digital sensed information and air quality parameter data from the I/O blocks within the routers or from the local sensors in the spaces back to the multipoint air sampling unit 200 is through data communications cable 201. The air transport media 202 can be constructed using the same materials mentioned previously for tubing 24A and other connections from the spaces 20 to the routers 300. The data communications cable 201 can be made with any commonly used data communications media such as twisted pair, shielded twisted pair, fiber optics cable or other. Additionally in a preferred embodiment the air transport media 202 and the data communications media 201 can be combined into one structured cable as was described for the connections between the rooms 20 and the routers 300.

As in FIG. 1 the multipoint air sampling unit 200 also connects to the Internet 170 to send information about the environments to a password protected website for review by the occupants or facility personnel. Again as in FIG. 1 the multipoint sampling unit 200 can also interface to and send data back and forth through data communications media 181 with the facility's building control or management system 180. This can be done directly or through one of many interface protocols such as BacNet, OPC, Lon by Echelon, XML or others.

In addition to the air and data routers 300 that can accept sensed input signals from the spaces 20 and provide signal output 31 to help control the rooms 20, the building control system 180 can also be used to accept various sensor input signals such as 29C from local room sensor 28C and signal 82 from room switch 81. This information can be used by the building control system directly for control and or communicated back to the multipoint air sampling system 200. For example, if the room sensor 28C was a temperature signal, this information could be detected by the building control system 180 and combined with absolute humidity or dew-point temperature information for room 20C, derived from the shared sensors 220 of the multipoint air sampling system, by either the building control system or the multipoint air sampling system to create a relative humidity or enthalpy measurement or signal for room 20C. The building control system 180 can also provide control signals to help control the airflow in rooms 20 as shown by signal 31C to the room airflow controller block 30C using shared sensor information from the multipoint air sampling system 100 or 200 and potentially locally sensed signals, room switch information, as well as other building information.

Figure 3:
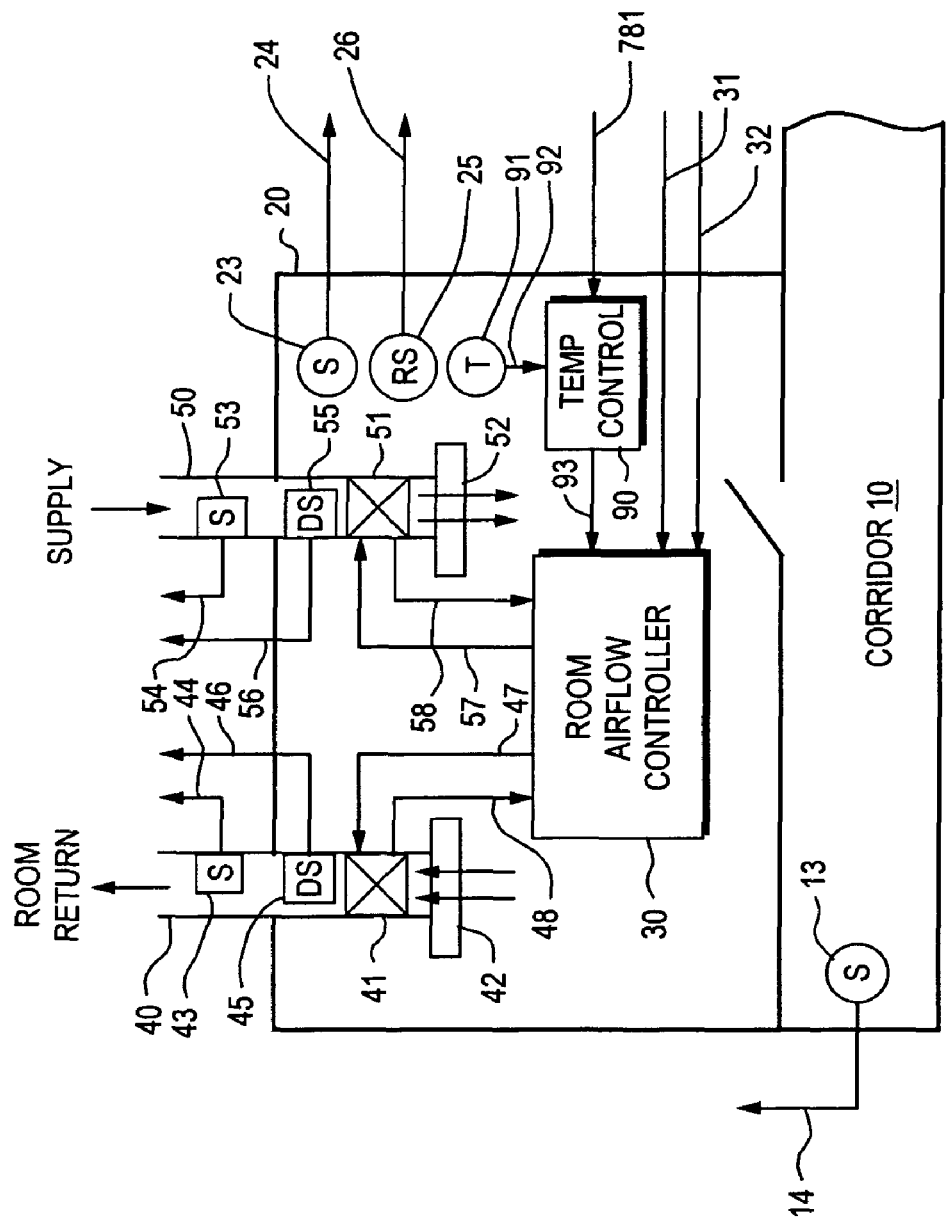
FIG. 3 is a detailed schematic diagram of a preferred embodiment of the system of the invention in a room.

FIG. 3 illustrates a more detailed diagram of one of the monitored areas that is controlled by a room airflow controller and some of the airflow control and feedback devices and signals used therein. Additionally, this diagram also includes a room return airflow sensing and control device 41 and return airflow control signal 47 as well as room return feedback signal 48. Supply airflow sensing and control device or devices 51 and supply airflow control signal 57 and supply airflow feedback signal 58 are also indicated.

Although a return airflow control device is indicated, most buildings will only have a supply airflow control device controlled by the room airflow controller. In these cases, the return air is uncontrolled and typically makes it way back to the air handling unit from the room or area via ceiling or other plenum spaces via an egg crate or other grill in the ceiling or air transfer duct from the room to the plenum space or a return air duct. Return airflow control devices are often used in those rooms where a certain pressure differential or airflow volume offset is desired between the room and surrounding rooms such as in an isolation room or operating room in a hospital, or a clean room. In other words an offset airflow is set between the return and supply flow so that the room is always slightly negative, neutral, or positive in airflow vs. surrounding areas based on the application. Additionally, in some cases if the room may contain hazardous contaminants or for other reasons, it may be desirable to completely exhaust the airflow from the room to outside. In this case, the room return may be ducted to exhaust fans completely exhausting the room air and making what is shown as a room return airflow control device effectively a room exhaust airflow control device with the control algorithms to control the device by the room airflow controller 30 being similar to that indicated in FIG. 5 for a room return airflow control device at least with respect to this simple situation.

Figure 5:
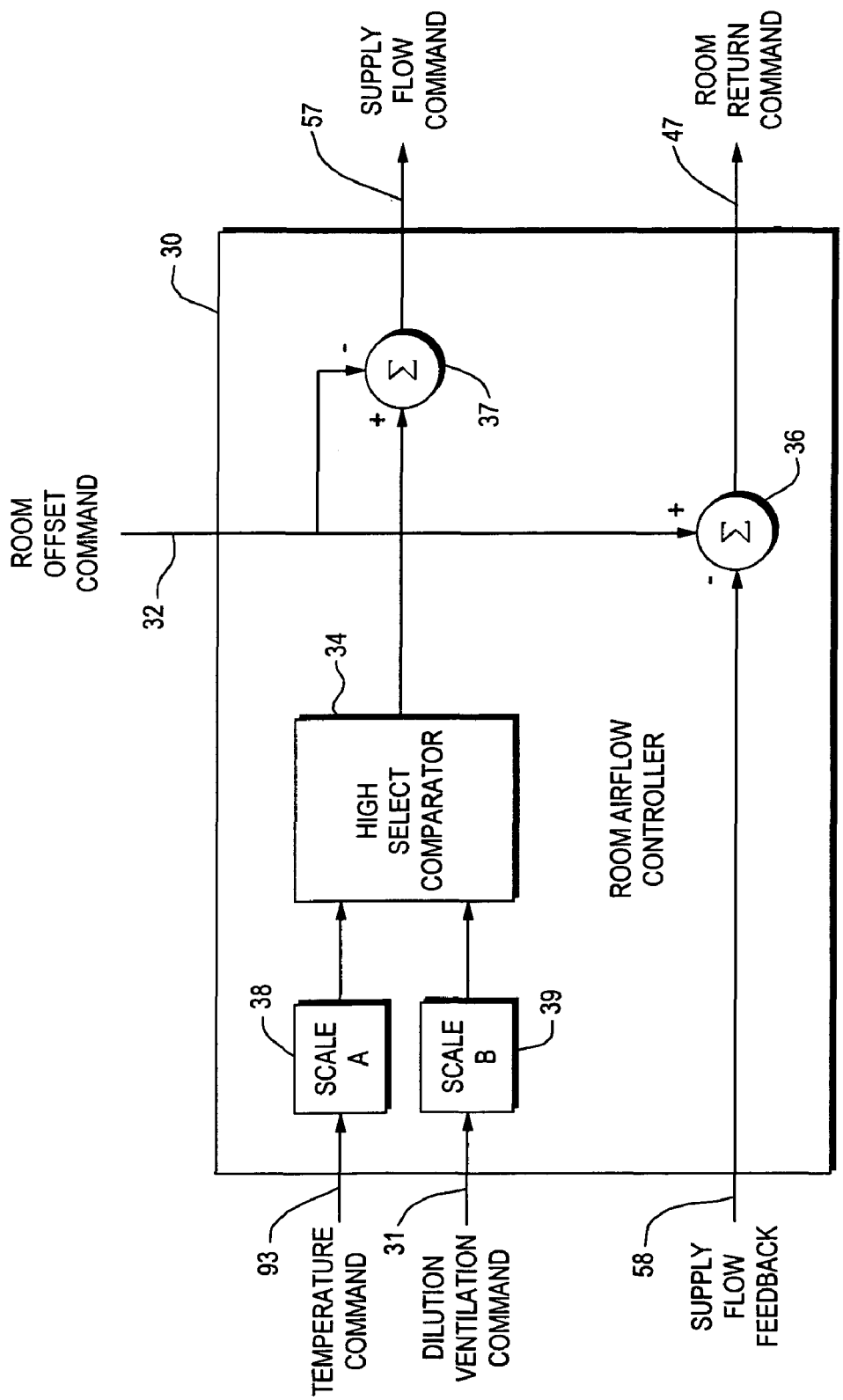
FIG. 5 is a schematic diagram of an embodiment of the room airflow controls logic of the invention for a space including a controlled room return airflow control device.

If no return airflow control device is present in the room or area that is controlled by room airflow controller 30, then FIG. 3 and the related control diagram FIG. 5 are still applicable except that the room return airflow control device 41 and its signals 47 and 48, plus room offset command 32 and supply flow feedback signal 58, should be omitted from the diagrams where they are indicated.

In FIG. 3, local temperature sensor 91 communicates through cable 92 to a temperature controller 90. This temperature controller could be part of building control system 180, a stand-alone system, part of the room airflow controller 30, or part of a separate system that controls the airflow in a space or room with a return or exhaust airflow control device. Such a latter control system that includes either a room return or room exhaust and supply airflow controller devices 41 and 51 respectively of FIG. 3, as well as the room airflow controller 30, and controls at least room pressurization by maintaining either a given room pressure or volume offset between the room and adjacent spaces is referred to in the context of this invention as a tracking airflow control system which may also be used for example in critical environments, laboratories, hospitals, vivariums, and various types of clean rooms. In this latter case the room airflow controller 30 may also be referred to in the context of this invention as a tracking airflow controller.

The purpose of temperature control block 90 is to provide regulation of room temperature which may involve sending a thermal load or temperature command 93 to the room airflow controller 30 to increase or decrease the volume of conditioned supply airflow into space 20. The temperature control 90 may also control a reheat coil to increase the temperature of the supply air fed into the space 20 or perimeter heating coils in space 20 for further means of temperature control.

FIG. 5 is an exemplary embodiment of the control diagram for the room airflow controller 30. The supply airflow is set by the higher of either 1) the room's temperature control signal that represents the room's supply airflow requirement to maintain proper room temperature or 2) the dilution ventilation command signal that represents the supply airflow requirements for dilution ventilation based on contaminant levels in the space plus in some cases the volume of supply air required to meet the space's occupancy based on the measurement of space carbon dioxide levels. The minimum override or high select function for these two signals is implemented as shown in FIG. 5 by high select comparator Block 34 which acts to take the higher of the two signals provided to it, passing which ever of the two signals is higher at any given time. The first input into high select block 34 is the scaled temperature command 93 for varying supply flow. This signal is scaled and potentially offset as needed in scaling block 38 to put it on the same scale factor as the other airflow command signal input into high select comparator 34, such as to a certain number of cfm per volt for an analog voltage signal or scaled directly into a given set of units such as cfm or liters per second for a software or firmware variable representing airflow. The second signal into block 34 is the dilution ventilation command signal 31 which is generated with the assistance of the multipoint air sampling system, or the building control system 180 and is again scaled and offset as needed by scaling block 39 to put this command on the same scale factor as the other signal.

The command 57 for the supply airflow control device 51 is further shown created by taking the output of the high select comparator block 34 and subtracting offset signal 32 from it by subtraction block 37. The room offset airflow command 32 could be a fixed offset setpoint such as 10% of the maximum supply or exhaust cfm, or it could be a signal from the building control system, multipoint air sampling system or the tracking airflow control system that varies in a two state, multi-state or VAV fashion. The purpose of this offset airflow signal or variable 32, if it is used, is to create a typically slight negative, positive, or neutral pressure for rooms employing a room return or room exhaust airflow control device. An exemplary application of the room offset airflow command 32 being a two state control signal is for signal 32 to be a value such as 10% of the maximum supply volume for normal room operation. However, when a cleaning compound or other spill, or other emergency condition is detected such as a fire or smoke release via some sensor, alarm system, or manually with room switch 81, the room offset airflow can be increased from its normal value by one of the controllers of the multipoint air sampling system 100 or 200, or the building control system 180. Increasing the offset airflow to a potentially much higher value for example will reduce the supply airflow volume so as to create a large negative offset airflow for the room to provide a measure of increased containment to prevent the spread of potential spill vapors or smoke into other spaces.

Finally FIG. 5 shows an embodiment of how command 47 for the room return or room exhaust airflow control device is created by first starting with the supply flow feedback signal 58. This signal 58 is next added to the room offset airflow command 32 by summation block 36. The resultant signal is the room return or exhaust command signal 47 that is used to set and control the flow of the room return or exhaust airflow control device 41.

If the space or room controlled by room airflow controller 30 has no return or exhaust control device 41, then there is no room offset command 32 or room return command 47. Furthermore, the supply flow command 57 simply equals the output of the high select comparator 34 with no subtraction block 37 required.

FIG. 6 shows a preferred embodiment of a multipoint air sampling system as applied to an air handling unit for monitoring and or control purposes. As shown in FIG. 6 return air 1001 for air handling unit 1000 comes for example from rooms 20 or other areas. As shown return air 1001 comes from return duct 40A from room 20A, as well as from plenum space 40C which is provided return air by transfer duct 40B from room 20B and ceiling grill 42C from room 20C. Return air may also come from other locations or areas in the building as shown by return duct or plenum space 40D. The supply air 1014 provided by air handling unit 1000 is provided to spaces in the building such as rooms 20A, 20B, and 20C through supply ducts 50A, 50B, and 50C respectively. Although not shown, other areas or rooms of the building such as for example corridor 10 may also be supplied by air handler unit 1000. Return air fan 1002 and supply air fan 1011 are used to move the air through the building. Prefilter 1016 is typically used in the location shown and is often a coarse filter that is used on the outside air stream. This is followed by a typically more effective and higher grade filter shown as filter 1008. Control of the temperature and humidity content of the supply air can for example be controlled through cooling coil 1012 and heating coil 1013. Other combinations of filters and heating and cooling coils used with respect to an air handling unit or similar roof top units for meeting various applications are well known to those skilled in the art of designing air handling units.

Additionally, the control of the amount of recirculated return air 1005, exhausted return air 1004, and outside air 1007 is through the control of exhaust air damper 1003, recirculated air damper 1006, and outside air damper 1067. These dampers can also be airflow control devices as defined earlier for such devices as 41A in FIG. 1 or 2, although the dampers or airflow control devices in FIG. 6 will typically be larger devices due to the larger air volumes involved. The control signals to control these dampers are shown in FIG. 6 as outside air damper control signal 1068, exhaust air damper control signal 1070, and recirculated air damper control signal 1072. There are many methods and algorithms known to those skilled in the art to control the relative positions of these dampers. Typically the building control system 180 or an air handler controls unit 1015 will control these dampers to meet various requirements of the building such as regarding the required amount of outside air, matters of energy efficiency relating to the heating and cooling of the building, and building pressurization.

To monitor the operation of the air handling unit 1000 and or to help control it more accurately, reliably and more cost effectively than has been possible with prior art systems particularly with respect to the control of the amount of required outside air, several air handler locations can be monitored with the use of a multipoint air sampling system such as that shown in FIG. 6 as block 1000. Multipoint air sampling system 1000 is shown for the purposes of illustration in FIG. 6 as a star configured multipoint air sampling system similar to that of multipoint air sampling system 100 in FIG. 1. However, the invention is equally applicable to a networked air sampling system such as that shown as blocks 200 and 300 in FIG. 2. Similarly, the invention could be used with a networked photonic sampling system.

To monitor most aspects of the operation of the air handler and to better control it, one of the preferred sense locations as shown in FIG. 6 involves sensing the return air 1002 either before or after the return fan with air sampling location 1031 and local duct sensor 1021 which is typically a temperature sensor for most applications. Another preferred sense location involves sensing the supply air typically after the fan and various heating and cooling coils to better ensure a more homogeneous distribution of temperature and air contaminants within the supply duct. This is shown in FIG. 6 with sampling location 1037 and local duct sensor 1027 which is also typically a temperature sensor. A previously mentioned sense location involves sensing outside air. In FIGS. 1 and 2 this is performed with sampling location 63 and local duct sensor 65. In FIG. 6 outside air 1007 is sensed for example in the outside air duct before the outside air damper 1067 and prefilter 1016 by air sampling location 1023 and local duct sensor 1033 which is typically a temperature sensor. Finally a location that may also be helpful to sense is in the mixed air plenum of the air handler where the mixed air 1009 of the air handler is present. This air is similar to the supply air but has not been filtered, heated or cooled by the air handler so it more closely reflects the mixed air quality parameter characteristics of the return air 1005 and outside air 1007. The mixed air 1009 is sensed by air sampling location 1035 and local duct sensor 1025 which is typically a temperature sensor for most applications. It is useful to note that care must be taken with the selection of the air sampling and duct sensor locations in the mixed air plenum. In many air handlers the return and outside air may be poorly mixed in the mixed air plenum before filter 1008 resulting in a non homogenous air contaminant and temperature distribution due to the different values present in the return and outside air.

With respect to the sensed duct locations, when multipoint air sampling systems are used to sample ductwork, plenums, air handlers or any other applications where flowing air in a partially contained area such as a duct or pipe is to be sampled and measured with a remote sensor, a tube or hollow duct probe may be inserted into the duct or partially contained space to withdraw a sample or else a hole can be made in the duct and a sample drawn from the duct from a tube connected to the opening in the duct wall. Additionally however, as noted above a separate temperature or other parameter or contaminant sensing probe or probes are also needed to make whatever local sensor measurements are desired from these ducts or partially enclosed areas. Multiple separate probes for both sensing the flowing air stream and for drawing air samples may be employed at these locations or a unique integrated sampling probe that uses one probe for both local air characteristic measurements and for air sampling may be used as described in the U.S. patent application Ser. No. 11/312,164, entitled "DUCT PROBE ASSEMBLY SYSTEM FOR MULTIPOINT AIR SAMPLING" which is incorporated herein by reference. This type of integrated duct probe or other nonintegrated duct probes may be used to sense any of the duct locations referred to in FIG. 1, 2 or 3. Additionally, this patent application also refers to the use of air sampling duct probes that use multiple sensing holes spread along a cross section of the duct to obtain a better average of duct conditions. This type of multiple pickup sampling probe plus an averaging duct temperature sensor that is also described in this latter patent application may be used advantageously for example to measure the mixed air 1009 of the air handler.

Figure 4:
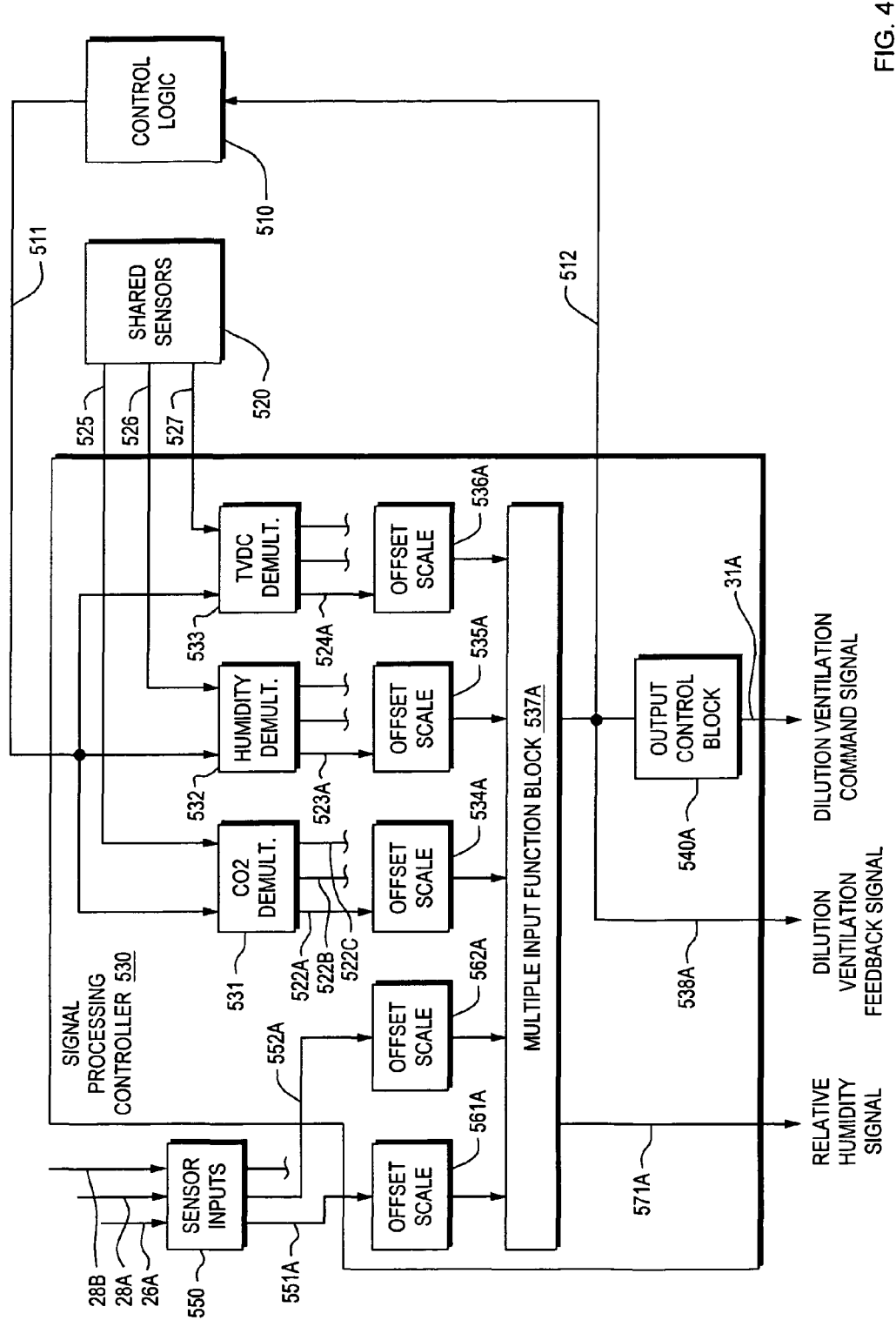
FIG. 4 is a schematic diagram of a portion of a preferred embodiment of the signal processing logic of the invention that may be used to create the dilution ventilation command signals.

As shown in FIG. 6 multipoint air sampling system 1100 accepts the four previously mentioned air sampling locations that are connected to the solenoid valves 1163, 1164, 1162, and 1161 by air sampling tubes 1032, 1034, 1036, and 1038 from sampling locations 1031, 1033, 1035, and 1037 respectively. This tubing is similar to the tubing 24A previously described with reference to FIGS. 1 and 2. The air quality parameters at these air handler locations are sensed by the shared sensors 1120 and processed by signal processing controller 1130 which can implement all the functions of FIG. 4 shown for signal processing controller 530. The solenoids 161 through 164 are also controlled by control logic block 1110. Finally multipoint air sampling system 1100 can accept local room or duct sensor signals or information through sensor inputs block 1150. This block senses local duct sensors 1031, 1033, 1035, and 1037 through cables 1032, 1034, 10356 and 1038 respectively. These cables are similar to the cable 26A described previously with respect to FIGS. 1 and 2. Alternatively, local duct sensors 1031, 1033, 1035, or 1037 may communicate their air quality parameter information to sensor inputs block 1150 through wireless or wireless network means such as a wireless mesh network.

Figure 9:
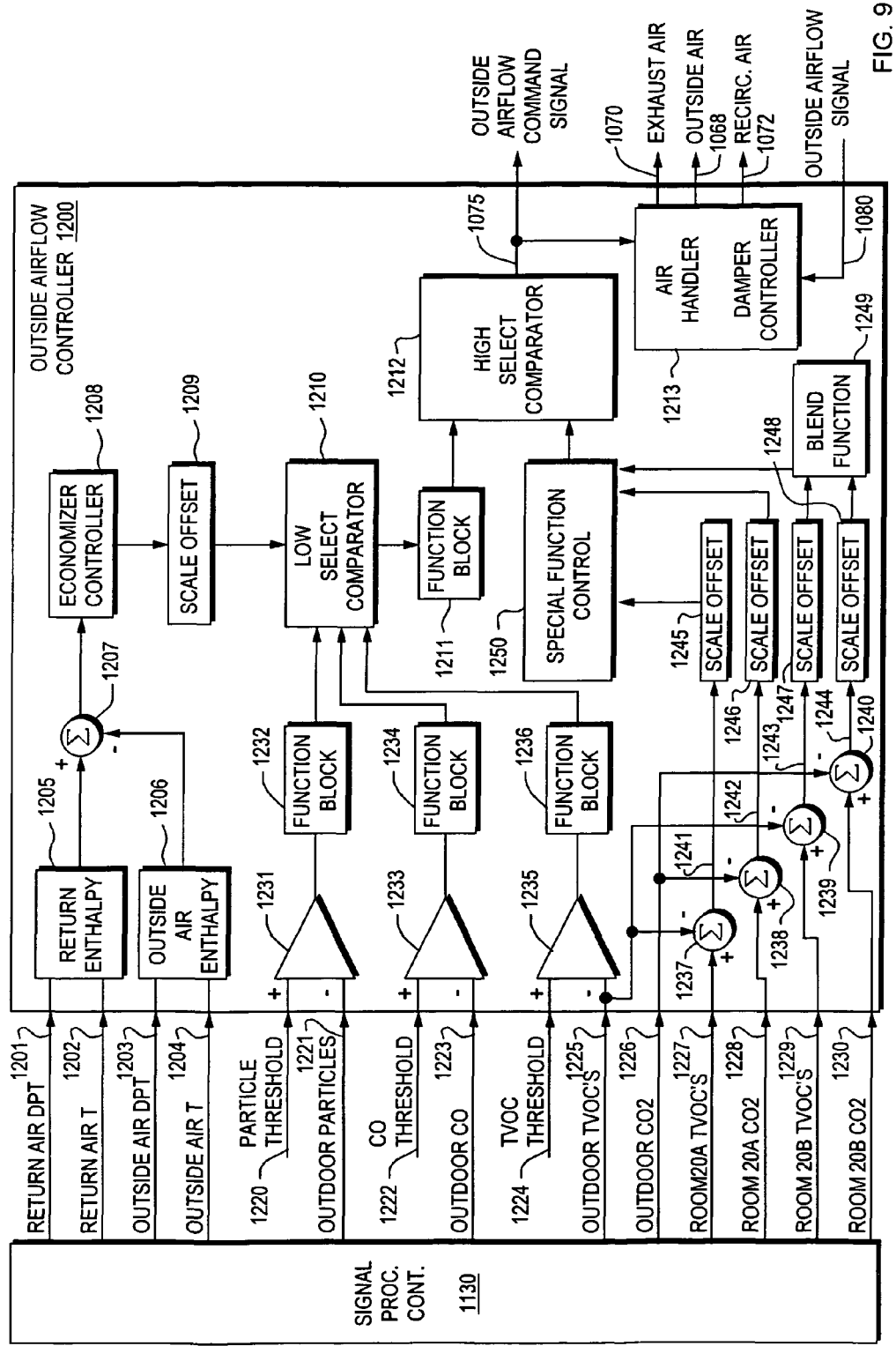
FIG. 9 is a schematic diagram of a portion of a preferred embodiment of the outside airflow controller logic of the invention that may be used to create the outside airflow command signals.

The control or monitoring signal outputs of signal processing controller 1130 can be provided for example to building control system 180 as shown, for control of the outside air damper 1067 or to other building systems or controllers such as the air handler controls block 1015 or more specifically to the outside airflow controller block 1200 which can be used to generate outside airflow command signal 1075 and is described in more detail through FIG. 9. Although not shown in FIG. 6, the building control system 180, the air handler controls block 1015, or another controller can be used to control the outside airflow into the building using outside air damper 1067 plus additionally the other air handler dampers 1003 and 1005 with the help of the outside airflow command signal 1075 from the outside airflow controller 1200.

Additionally any of the control or sensing approaches, or control inputs or outputs mentioned in FIGS. 1, 2, and 6 can be applied to the system or approach of the other figures. Similarly these same approaches or systems can be applied to a facility monitoring system embodiment similar to that of either FIG. 1, 2, or 6 that are implemented not with a multipoint air sampling system but instead using a fiber optic light packet sampling and sensing system such as described in U.S. Pat. No. 6,252,689 and referred to in this patent as a networked photonic sampling system.

The creation of blended air quality parameter signals involving the use of multipoint air or photonic sampling systems begins with the creation of a virtual air quality parameter signal that is creating by de-multiplexing the sensor stream signals of the shared sensors blocks 120, 220, 520, or 1120 of FIG. 1, 2, 4, or 6 which is performed by the signal processing controller block 130, 210, 530, or 1100 in FIG. 1, 2, 4, or 6 respectively. An implementation of a portion of the signal processing logic of the signal processing controller block that does this de-multiplexing plus other functions is shown in signal processing controller block 530 in FIG. 4. In this diagram the control functions can be implemented in analog or digital logic or be implemented with computer software or a firmware program or any combination of these. In FIG. 4, shared sensors 520 create one or a multiple of output signals or variables shown for example in the diagram as sensor signals 525, 526, and 527 representing the outputs of individual sensors $CO_2$, humidity (such as for example measured as dewpoint temperature, absolute humidity, or water vapor concentration), and TVOC's respectively. Although FIG. 4 illustrates the use of these three sensors, any number or type of sensors can be used. Since the sensors are being multiplexed with the air samples from multiple rooms, three in this example, the individual or "virtual" sensor signals for a given room corresponding to, as mentioned previously, a sensor signal or represented software variable for a given air quality parameter in that room or area must be de-multiplexed from the signal stream of that air quality parameter. This is done within signal processing controller 530 by the de-multiplexers 531, 532 and 533 that de-multiplex the CO2, humidity, and TVOC sensor signals respectively using the control signals 511 from the control logic block 510. Block 510 corresponds to control logic block 110 and 1100 in FIGS. 1 and 6 respectively, as well as part of signal processing controller block 210 and part of control logic block 310A, B, and C in FIG. 2. The output of the de-multiplexing blocks 531, 532, and 533 are individual or "virtual" sensor signals or software variables that represent the sensed air quality parameters for rooms 20A, B and C. For example, signals 522A, B and C represent the signals or variables for the sensed CO2 levels in rooms 20A, 20B and 20C, respectively.

These virtual sensor signals will typically have a value representing the last de-multiplexed value that will be held constant at that level until the next sampling of the corresponding location for that signal which may occur every few minutes or more likely every 10 to 30 minutes based on the needs of the application. At this point the signal will change value to equal the new de-multiplexed value. This transition of state from one de-multiplexed value to the next de-multiplexed value can occur either as a rapid or approximately step change in signal or it may occur gradually in a ramped manner lasting from several seconds in time up to many minutes depending on the desired properties of the virtual signal, what may be being controlled with that signal, and how often the location is being sampled. A preferred approach for signals used for control applications would be to have a gradual change of value occurring over between 5 and 60 seconds.

If we again focus on the variables for Room 20A, then the signals for CO2, humidity, and TVOC are 522A, 523A, and 524A respectively. As mentioned previously these individual or virtual sensor signals 522A, 523A, and 524A can then be modified with an offset and scale factor block 534A, 535A, and 536A respectively as needed or some other control function can then be applied. Additionally, sensor inputs block 550 has as its inputs local room or duct sensors which for example in FIGS. 1 and 2 are shown as 25A, 27A and 27B. The signals from these sensors, 26A, 28A, and 28B are applied to the sensor inputs block 550 which may buffer them and then provide these signals to the signal processing controller 530. In particular for room 20A, signals 551A represents the signal from local temperature sensor 25A and signal 552A represents the signal from local room sensor 27A. As with the virtual signals the local sensor signals 551A and 552A can then be modified by offset and scale factor blocks 561A and 562A respectively as needed or by some other function other than or in addition to an offset and scaling function which typically provides the function of Y=AX+B where Y is the output and X is the input. The modified signals from blocks 534A, 535A, 536A, 561A, and 562A are then acted upon by multiple input function block 537A which in this example generally involves signals associated with room 20A. Alternatively, air quality parameter signals from other areas or duct locations could be used as well by multiple input function block 537A such as for creating differential signal versions of some of the air quality parameter signals. Additionally, although not shown in FIG. 4 the signal processing controller can contain many multiple input function blocks implemented with hardware or with firmware, software, or a combination thereof to create various blended air quality parameter signals for other spaces or rooms. The output signals from multiple input function block 537A such as dilution ventilation feedback signal 538A may be further processed or modified by output control block 540A to for example generate an output command signal such as dilution ventilation command signal 31. For example control loop functionality such as shown in FIG. 8 or a threshold level comparator with or without hysteresis such as that shown in FIG. 7 can be used in output control block 540A vs. in function block 537A to convert a blended air quality parameter feedback signal produced by the multiple input function block 537A into a command signal output that can be used to control a minimum supply airflow level for dilution ventilation or other purposes.

The multiple input function block 537A may also have multiple outputs as shown in FIG. 4 where a second output 571A is shown which is a blended monitoring or feedback control signal for relative humidity. The absolute humidity or dewpoint output 523A can be combined with local temperature sensor output 551A using commonly known psychrometric equations to create the relative humidity signal 571A or if desired other moisture related signals such as wet bulb temperature or enthalpy. This blended relative humidity signal 571A can be used for monitoring or as a feedback signal that can be used by another controller to control relative humidity levels in the space 20A or by another output control block similar to 540A to create a relative humidity command signal all from within the signal processing controller 530.

Describing multiple input function block 537A in more detail, this block may for example add signal inputs together; take the difference between different signals such as to create differential signals; high select or take the higher of various signals; low select or override various signals; apply threshold value or signal pattern trigger functions to the signals either individually, as a group, or as subgroups to modify or create new signals; apply control loop functionality similar to output control block 540A as is shown in FIG. 8; apply hysteresis functions as shown in FIG. 7; apply any Boolean logic, linear, or nonlinear function; or apply any other function or approach of benefit to blend or use these signals to create blended monitoring or control signals. The result of block 537A is to create one or more of two state, three or multiple state, or continuously variable blended air quality parameter signals that can be used as the basis for dilution ventilation feedback, dilution ventilation command, outside air command, and other monitoring or control feedback signals. Finally, this command or feedback signal or control variable may then be outputted to a building control system or to another system as either a digital signal or variable such as dilution ventilation feedback signal 538A or as an airflow command signal or software variable such as the dilution ventilation airflow command signal 31A created by output control block 540A and used as an input to room 20A's environments airflow control block 30A.

One other function that may be implemented within multiple input function block 537A or potentially in output control block 540A is a time delay or ramp function which is most applicable when a discontinuous output signal is created such as two state, three state or multiple state signal that is to be used in a control system. Since many control systems may not respond in a stable manner to rapidly changing signals it may be helpful in some situations to effectively create a continuously variable signal out of a multiple state signal. For example, when a threshold value for a given air quality parameter signal or blended air quality parameter is exceeded, the output of function block 537A or 540A could be increased to it's maximum or purge value that might correspond for example to a room air change level of between 5 to 15 ACH's. This increase in value can occur instantly or may be commanded to be a gradual ramp by function block 537A or 540A. Such a ramp or slowly increasing signal could occur over the span of a minute or more. This action may also be helpful to prevent problems with the control system or the airflow control devices trying unsuccessfully to keep up with a rapidly changing signal that could cause a pressurization problem in the case of a space with a return or exhaust airflow control device such as in room 20A, if the supply and return airflow control devices do not properly track the changing airflow command signals. Similarly, when the dilution ventilation command signal is meant to drop from a higher level such as 10 ACH down to a lower or minimum level such as 2 ACH, the function block 537A could create a slow ramp that gradually decreases the output signal 31A over some period of time such as one minute or more.

Similarly these increasing or decreasing ramps or gradual changes in level could be made linear, with constantly increasing or decreasing rates or made non-linear such as with an exponentially changing rate so the ramp could start faster and gradually slow down or conversely start slowly and gradually increase its rate of change in value until the signal hits it final value. These ramps could also be at different rates based on whether the signal is increasing or decreasing. For example, it may be advantageous to rapidly increase the ventilation of a room by rapidly increasing the dilution ventilation command 31 if a large increase in the air quality parameter level in the room is detected. For example, a spill may have occurred with a cleaning compound. However, it may also be helpful to have a slow ramp downward; perhaps taking 5 to 15 minutes to gradually come down in dilution ventilation flow to make sure that the air quality parameter is removed even to a level below the threshold of detection.

In an alternative to ramping the changing flow over a large signal range, it may, for the same reasons mentioned above, be desirable to change not just the rate of change of the output of block 537A or 540A such as for the dilution ventilation command signal 31, but also the amount of the step change possible based on a change in the sensed air quality parameters such as from the shared de-multiplexed sensor signals 522A, 523A, and or 524A. In other words, rather than allow a full slew from the minimum dilution rate to the maximum dilution rate from one air sample measurement, it may be desirable to limit the maximum step change in dilution ventilation airflow or effectively impose a slew rate limit on how fast a rate the signal output of block 537A or 540A can change. The advantage of limiting the step size or slew rate of the output signal is that for normal variations in the signal amplitude, very little delay is created by this approach leading to more stable control. As an example of this approach, a maximum step change size could be set for an increase in airflow representing two ACHs in a possible range from a minimum of two ACH to a maximum of eight ACH. With the maximum step size set for example for two ACH, it would take three successive air samples to have air quality parameter values in excess of the trigger values to boost the dilution ventilation command signal 31 from the minimum to it's maximum value. Similarly, if the maximum reduction was also limited to a flow rate equal to two AC it would take three successive measurements of the environment's air quality parameters to be below the trigger value for the dilution command level to drop from a level corresponding to eight ACHs down to two ACH.

In a manner similar to the ramp approach mentioned above, the increasing and decreasing step heights may be of different sizes. For example, to respond quickly to a cleaning chemical spill there may be no limit or a larger limit for an upward or increasing change in dilution ventilation command signal 31. However, to ensure a large amount of dilution to very low levels and reduce the possibility of an oscillation if the source is not a spill, but a continuous emission, it may be advantageous to have a smaller decreasing step change size to hold the dilution ventilation at a higher level for longer periods so it takes several air sample cycles to fully reduce the ventilation level to its minimum level.

Another means to set the step heights or possibly the ramp rates is based on the level of detected air quality parameters or their rate of change. If a large value of an air quality parameter and or a rapid rise in its level is detected since the last sample or recent samples, it may be advantageous to use different step change heights or ramp rates. For example in a spill, where there is a sudden increase to a large air quality parameter value, it may be prudent to immediately index the dilution ventilation command signal 31 to its maximum value. Smaller or more gradual increases in value could be used when the sensed air quality parameter moves with smaller steps or more gradual changes. On the other hand a sharp downward change in the sensed air quality parameter or blended signal might not change the downward step level in order to keep the ventilation higher for a longer period of time to better clean the air. Alternatively, for energy saving reasons and or if there happens to be many brief upward excursions of air quality parameter levels that may not be hazardous, it may be more beneficial, if the air quality parameter level has just rapidly dropped to below the trigger level to quickly drop the dilution ventilation command signal 31 to its minimum level. As such, it may also be beneficial to have different step or output characteristics associated with each air quality parameter. As a result, the output control characteristics would be different based on which air quality parameter(s) triggered the need for more dilution ventilation.

Output signals of the signal processing controller block 530 may also be used to change the sampling sequence based on the detection of a spill, rapid increase in one of the air contaminants, or a level of an air quality parameter that is of interest to more closely observe. In this alternate approach the sequencing of air samples into the shared sensors from the environments 20 may be altered through signal processing controller block output signal 512 that is used by control logic block 510 to modify the sampling sequence on a potentially temporary basis during the period of a detected event of interest in a particular space 20. Based on seeing the control signal or software variable 512 increase in value to some higher trigger level or exhibit some signal pattern such as a rapid rise in amplitude, the control logic block 510 might increase the frequency of the air sampling of the space where the event was detected. Alternatively or additionally, the areas around the affected space may be quickly sampled next or sampled at a higher frequency as well to look for a spread of the air contaminant to other spaces. In the context of this invention a rapid rise in amplitude can be defined as a sudden increase in value to a level such as many times larger than the normal trigger level in less than 5 minutes such as that seen due to a spill of a volatile organic compound such as a cleaning compound.

This change in sampling or control sequence can be implemented with the sampling system of either FIG. 1, FIG. 2, or FIG. 6. If the system of FIG. 2 was being used for example, the detection of the event would be most likely carried out by the signal processing controller block 210 and the change in sequencing carried out by control logic blocks 310A, 310B, 310C and 310D.

Another change in control sequence that could be implemented if an event of some type is detected in a space or several spaces would be to change the sampling sequence by adding air sampling of several spaces at once to measure a mixed sample of several rooms. This could be implemented for example, by turning on one or more solenoids at once to gather a mixed sample of affected areas or of multiple areas nearby the affected area to rapidly look for potential spillage into other areas. This would be implemented in the same manner as mentioned above but would involve turning on multiple solenoid valves such as for example solenoids 161, 162, 263, and 164 in FIG. 1 or solenoids 361A, 362A, 363A, and 361B in FIG. 2.

There are several different approaches that can be used for creating blended or composite air quality parameter signals that can be used for monitoring only or for control purposes such as for example the dilution ventilation command signal 31 or the outside air command signal 1075. These blended signals can be implemented at least in part by the signal processing controller blocks 130, 210, 530 or 1130 of FIG. 1 2, 4, or 6 respectively, building control system 180, or output control block 540A of FIG. 4 and outside airflow controller 1200 of FIGS. 6 and 9. These blended signals, particularly the signals used for control, have two important aspects. One component refers to the signal type, which also impacts the control approach, such as two state, three or multiple states, continuously variable, or signal or control approaches that involve a combination of both discontinuous and continuous functions. The other aspect refers to the makeup of the signal or how multiple sensor signals are combined or blended to generate air quality parameter feedback or monitoring signals as well as ventilation, outside air or other control and command signals.

One embodiment of a blended air quality parameter signal that can be used for example for the dilution ventilation command signal 31 is a two state control signal whereby dilution ventilation command signal 31 is maintained at it's minimum level, for example at a dilution ventilation value corresponding to, for example, 2 or 4 ACH (or some other appropriate lower value depending on what's suitable for the environment being monitored), unless a trigger event occurs that could consist of a threshold or trigger value being exceeded by the sensor signal, particularly that of an air contaminant sensor such as for example TVOC's, CO, or particles. If the sensor signal were to consist of just one air quality parameter, a simple threshold or trigger value (corresponding to the value of the sensed air quality parameter at which some action is to be taken) can be defined. Alternatively, the trigger could consist of the signal matching in some way a specified signal pattern such as a rapid increase in level even though a specified threshold level was not achieved. The trigger event could also consist of a combination of one or more sets of threshold values and signal pattern pairs, any one of which could constitute a trigger event.

If more typically, multiple sensor air quality parameters are being employed such as from the shared sensors 120 and or a local room sensors 25A, the trigger event could be defined as any one of the employed sensor signals exceeding a threshold value, matching a signal pattern, or meeting the conditions of one of potentially multiple sets of threshold level and signal pattern pairs. Each sensor signal would most likely have a different threshold value level and or signal pattern that corresponds to an appropriate value for the sensed air quality parameter based on accepted levels of that signal related to one or a combination of health, comfort or other criteria of importance for that sensed air quality parameter. For example, a PID TVOC sensor would likely have a threshold level of about 0.5 to 2 PPM. A level in this range senses many materials below their OSHA TLV (Threshold Limit Value) while still not generating many false alarms by staying above normal levels of less harmful materials such as alcohol vapors. If a particle counter measuring in the range of 0.3 to 2.5 microns is used a level can be set that would not normally be exceeded such as in the range of 1.0 to 5 million particles per cubic feet, yet still pick up the evolution of smoke or some type of aerosol generated by some event in a monitored space. The specific level could be set based on the level of filtration to the space, i.e. the more the filtration, the lower the level that could be used. Other sensors such as a carbon monoxide, ammonia, nitrous oxide, ozone, or other toxic gas sensor can be set directly for the TLV of the compound or for a lower level that would not normally be reached in typical operation. Although CO2 based demand control ventilation is typically done with a continuously acting or variable signal a simpler form of control can also be achieved by increasing ventilation when the CO2 levels in a room exceed some threshold level such as 1000 PPM, or a value in the range of 800 PPM to 1500 PPM of CO2, or a value of 400 to 1000 PPM above the ambient outdoor concentration of CO2. These threshold values of CO2 do not refer in any way to health limits of CO2 since CO2 is in almost all situations not considered a harmful air contaminant, but instead is a proxy for adequate rates of outside air per person since the differential value of CO2 in a space vs. outdoor levels also refers to the amount of outside air ventilation in a space divided by the number of people, sometimes referred to as cfm outside air per person. The engineering organization ASHRAE (Association of Heating, Refrigeration, and Air Conditioning Engineers) has set various guidelines for values of outside air ventilation that vary for different types of facilities but are generally desired to be in the range of 12 to 25 cfm per person which corresponds to between about 425 PPM to about 875 PPM above ambient levels outside the building which can typically be between 300 and 500 PPM.

Alternatively, a triggering condition could consist of a combination of two or more sensed air quality parameters each reaching or exceeding a given level for that compound or meeting some signal pattern condition. For example, individually, a moderate level of fine particles such as 1.5 million particles per cubic feet, a moderate level of TVOC's such as 0.5 PPM, or a moderate level of temperature excursion to above 85 degrees might in themselves not trigger a need for increased dilution ventilation. However, the combination of all three air quality parameters meeting the preceding conditions could indicate a fire or explosion that would definitely require an increased level of ventilation.

A further implementation of a trigger condition involving multiple sensed air quality parameters could instead consist of an additive trigger condition. A good example of this relates to exposure to hazardous materials. OSHA indicates that the effective TLV of a mixture of gases can be computed by adding the fractions of each individual compound's level vs. it's TLV to get the fraction of the combined mixture against the combined TLV. For example, if the system detects that carbon monoxide is at 65% of the threshold limit value and that sulfur dioxide is sensed to be at 70% of its TLV value then although individually neither compound would trigger the system the combination of the two would be at 135% of the combined TLV and as such would constitute a trigger condition. To implement this approach each sensed air quality parameter of interest would be individually scaled based on its threshold value and then added together and a threshold trigger set for the summed result.

For example, this could be implemented by first choosing a leading parameter to perform ventilation control off of (CO2, for example) and then scaling the other parameters (particles, TVOC's, etc.) to be included in the composite feedback signal based on the ratio of the trigger level of the leading parameter to that of the additional parameter. For example, if CO2 is the leading parameter with a trigger level (setpoint) of 1000 ppm and TVOC's is a secondary parameter with a trigger level of 30 ppm the multiplier which "normalizes' or scales TVOC's to CO2 in this case is:

$$\frac{1000 ppm}{30 ppm} = 33.33$$

With these conditions, the TVOC reading is multiplied by 33.33 and then added to the CO2 signal, so that a controller with a setpoint or trigger point of 1000 ppm for CO2 may be used to limit TVOC's to 30 ppm. Alternatively, the two signals can be high selected to each other to create a blended air quality parameter signal that can then be compared to a signal threshold level or control setpoint for simpler operation.

Another variation on how a trigger condition can be set up is to have the trigger condition for one of more sensed air quality parameters vary or be changed based on some other air quality parameter or some other condition of the space. For example, a trigger condition could be varied based on occupancy, if no one is in the space, the trigger conditions for some air quality parameters might be raised slightly to save more energy by permitting a lower ventilation rate and higher contaminant levels for unoccupied periods. The trigger level could then be lowered when someone is detected or determined in some way to be in the space through, for example, an occupancy sensor or light switch, a card access system, or other means such as the detection of changes in CO2 in the space. There could also be manual local, or remote override changes to the trigger levels, based on for example, an increased or decreased concern about the air quality parameters in the room or space. Alternatively, the levels could be changed automatically by the signal processing controller 130, 210, 530, or 1130 of FIG. 1, 2, 4, or 6 respectively, some other system such as the building automation or building control system 180, or a tracking airflow control system.

Finally, any number of different logical or Boolean combinations of sensed air quality parameter values or sensor signal pattern conditions acting on any number of sensed air quality parameters affected by any other set of conditions or acted upon by other systems can be used to create a blended air quality parameter signal that can be used with the appropriate trigger conditions to create a two state blended feedback signal that can call for increased dilution ventilation by increasing dilution ventilation command 31.

There are a vast number of control techniques that may be used to generate command 31 using for example output control block 540A in order to vary the amount of ventilation within the monitored environment 20 in order to dilute the sensed air quality parameter sufficiently to prevent the concentration of the airborne air quality parameter from exceeding a specific level. Any method that one may use, from a standpoint of control logic or algorithm, whether it be an open or closed loop strategy involving continuous or discontinuous control functions, fuzzy logic, proportional-integral-derivative functions, feed-forward functions, adaptive control, or other techniques known to those skilled in the art of control system design, are considered to be aspects of this invention.

Figure 7A:
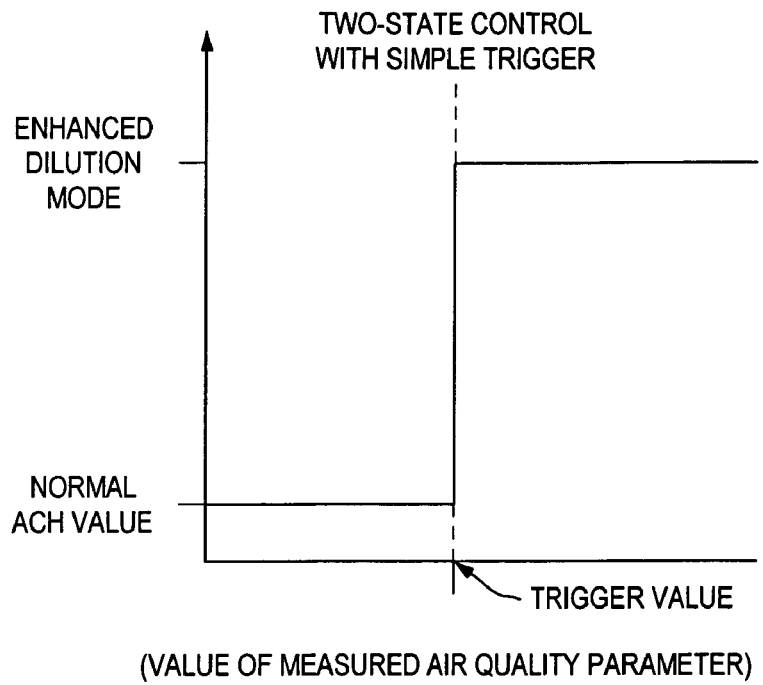
FIGS. 7A and 7B are schematic diagrams of various steady-state levels associated with air change rate control sequences.

FIG. 7A illustrates one possible scenario of steady-state levels associated with command 31 when signal processing controller 130 is configured to provide a two-state control function such that dilution ventilation command signal 31 is increased to an enhanced dilution mode level from a normal level or ACH (air changes per hour) value when a blended or composite air quality parameter signal or signals created by function block 537A for example relating to environment 20 transition above an established trigger value or values. Conversely, when the value of the blended air quality parameter signal or signals transition from a level that's above the appropriate trigger value to one below that value, command 31 will drop back to its normal steady state airflow or ACH value. FIG. 7A makes no reference to the time response of command 31 as it transitions from the normal ACH value to the Enhanced Dilution mode and vice versa, as this is a function of the particular control technique used to make such a transition while ensuring that stability is maintained within the system. As an embodiment of this invention the two-state approach of FIG. 7A can be acceptable for use in many applications. However, in some cases the system stability realized with the simple switching mechanism depicted by FIG. 7A will benefit by including provisions to prevent command 31 or other commands such as outside air command signal 1075 from oscillating.

As an embodiment of this invention, when command 31 is transitioned from the normal ACH value (1-4 ACH, for example) to the enhanced dilution mode (10-15 ACH, for example), command 31 will be latched or become fixed at that higher value by for example output control block 540A, so that following the transition if the measured air quality parameter drops below the triggered value the air change rate will remain high. Such an approach may be accompanied by some form of notification mechanism from the Building Control System 180, or the sampling system 100, 300, 400, 1100 or via the interne connection 171, or from the air flow controller 30 or some other component of the system that airflow controller 30 connects to, which will alert maintenance personnel or other staff that the trigger value has been exceeded so that signal processing controller may be manually reset.

Figure 7B:
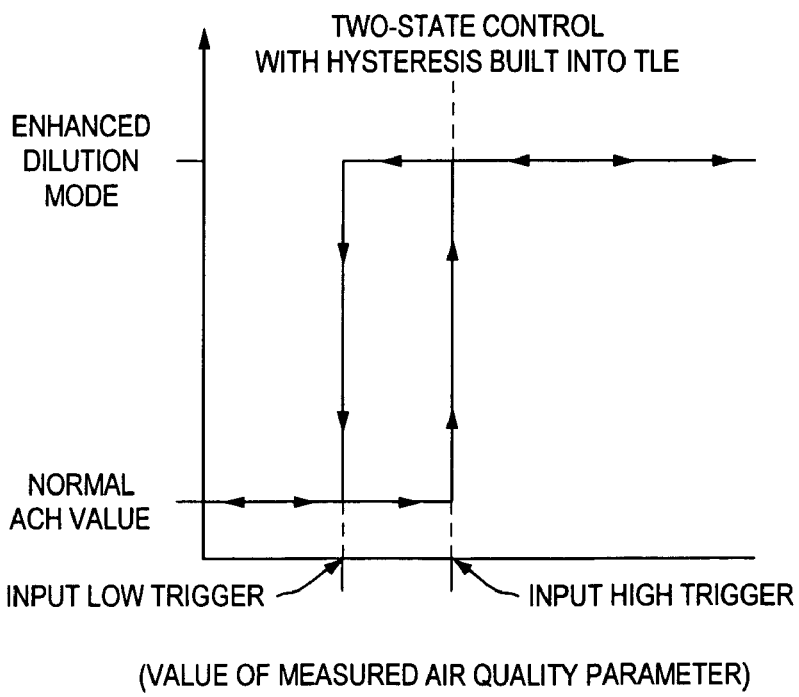

As an alternate embodiment, instead of latching command 31 when the value of the sensed or blended air quality parameter exceeds an established trigger value, one may apply a hysteresis function as shown in FIG. 7B which depicts another scenario of steady-state levels associated with for example command 31, in which two different triggers or transition points are provided (input low trigger and input high trigger). Here the input high trigger is used when the command 31 is at a level corresponding to the normal ACH value, while the input low trigger is used when the command 31 is at a level corresponding to the enhanced dilution mode.

A preferred signal type and resultant control approach for dilution ventilation command signals 31 or other blended monitoring or control signals derived from air quality parameter signals involves using three state signals to implement a three state control approach. Unlike the previously mentioned signal type and control approach, which had two output levels such as a high level, typically for a purge, and a low normal operating level, this approach has three output levels. A typical application for these three levels would be the same two levels mentioned previously with an intermediate level added that is not for spills (an extreme transgression in the levels of a sensed air quality parameter) but for controlling more moderate levels of sensed air quality parameters that are desired to be lowered. For example, if a level of between 1 PPM and 10 PPM from the TVOC detector is sensed, the system would increment up a moderate level, say from a minimum level of 3 ACH to a level of 6 ACH's. However if the TVOC detector sensed levels above 10 PPM, then the system would go into a purge mode with perhaps 10 to 15 ACH's of dilution ventilation. This approach limits energy consumption for moderate air quality parameter levels and reduces the chance that if multiple rooms are at this moderate level, that the total system airflow capacity of the building will be exceeded by too many rooms being commanded to maximum air change rate (ACH) value. Another benefit of a three or other multiple level approach (or of a VAV approach as well) is that it lessens the chance of realizing an unstable condition where the room airflow can vary up and down due to a steady release of air quality parameters that alternately is purged to a low value and then slowly builds back up as the system alternately increases and overshoots and then decreases and undershoots the desired dilution airflow command level by an amount that exceeds what is required for a stable operating condition.

The three state control approaches can be extended beyond three output states to any number of output states for dilution ventilation command signals 31 to provide different levels of dilution ventilation for a space. Finally any of the approaches to use multiple sensed signals such as from the shared sensors 120 and or a local room sensors 25A can as mentioned previously for the two state approach, also be used for the three or other multiple state control approaches with the addition of another set or additional sets of trigger levels and comparators for the intermediate or other output signal states. Additionally, the output of the comparators from multiple parameters can be added together so that for example if the first or intermediate thresholds for two air quality parameters are crossed then the output signal is indexed to the maximum flow or signal state for a three state signal or to the third flow level or signal state in a multiple flow or multiple state air quality parameter signal vs. to only the second or intermediate level. Additionally there may be some air quality parameters due to their hazard levels that even crossing the "first" threshold level requires the use of much higher or potentially maximum flow or signal state with no or less other intermediate threshold or trigger levels needed. Alternatively, in a preferred embodiment the air quality parameters can be scaled to each other and then added together as mentioned previously to create a blended air quality parameter signal that can be compared to just one set of two or more threshold levels. This latter approach is convenient for multiple output states or when it is desired to change the threshold levels, requiring only one set of thresholds to be modified.

Another preferred type of signal and related control approach for creating and using blended air quality parameter signals such as dilution ventilation command signals 31 is to use continuously variable signals that can be used to implement a variable air volume or VAV control approach. With this signal type and control approach, once the sensed air quality parameter signals reach some trigger level or match some signal pattern, the dilution ventilation command signal 31 or the corresponding dilution ventilation feedback signal 538A can increase in a continuous manner from a minimum level which would match the minimum state output of the two or multiple state approach, all the way up to a maximum level that would correspond to the maximum level of the two state or multiple state approach. This effectively "infinite state" approach can be implemented as mentioned with the previous control approaches by creating a blended air quality parameter signal from a plurality of sensed air quality signals such as from the shared sensors 120 and or local room sensors such as 25A that can be blended or combined in any manner. As before the individual air quality parameter signals can be acted on individually and then added or high selected to form the blended resultant signal. However, with continuously variable signals it is usually preferable to first add or high select the scaled, offset or other wise modified air quality parameter signals such as from the outputs from scale and offset blocks 561A, 562A, 534A, 535A, or 536A of FIG. 4 with for example the multiple input function block 537A before applying control loop, hysteresis or other functions to for example the blended feedback signal 538A with output control block 540A of FIG. 4. Additionally, multiple input function block 537A can also apply override or low select functions between the inputted air quality parameter signals or apply other linear, nonlinear or Boolean logic functions to the individually scaled signals before or after combining these signals.

Output control block 540A can also apply linear or nonlinear functions to the blended air quality parameter signals such as 538A. For example with a linear relationship an offset and simple scale or gain factor can be used as well as a minimum and maximum clamp so that as the dilution ventilation feedback signal 538A increases above the minimum command signal value, the dilution ventilation command signal 31 will increase as well until it hits the maximum allowed command signal value. Another of the reasons to use a continuously variable signal state is to create closed loop control of the indoor environmental quality within the monitored space or building so as to prevent an oscillating control pattern that might be generated in some situations by a two state or even a multi-state approach. With a continuously variable signal state a variable air volume (VAV) control approach can be implemented so that an increased ventilation level can be maintained in a stable manner between the minimum and maximum command signal levels, particularly where there is a roughly constant level of air quality parameter emission. This approach could be used to regulate the level of an air quality parameter such as a TVOC, particulate, or other at a certain setpoint rather than drive it to a minimum level that could prove to be costly in terms of the energy expense of running at high ventilation for extended periods. This approach is also appropriate when the air quality parameter is not a particularly hazardous one and can be set to be maintained at a level that would not create a health impact such as with particles. More particularly, by using a blended air quality parameter signal consisting of a plurality of air quality parameters, the quality in a space can be maintained to a "cleanliness level" that incorporates the control of many air quality parameters within one system or even one control loop. In this approach where the blended air quality feedback signal can be controlled to a setpoint value representing a measure of the combined state or cleanliness of the air in a space.

Figure 8A:
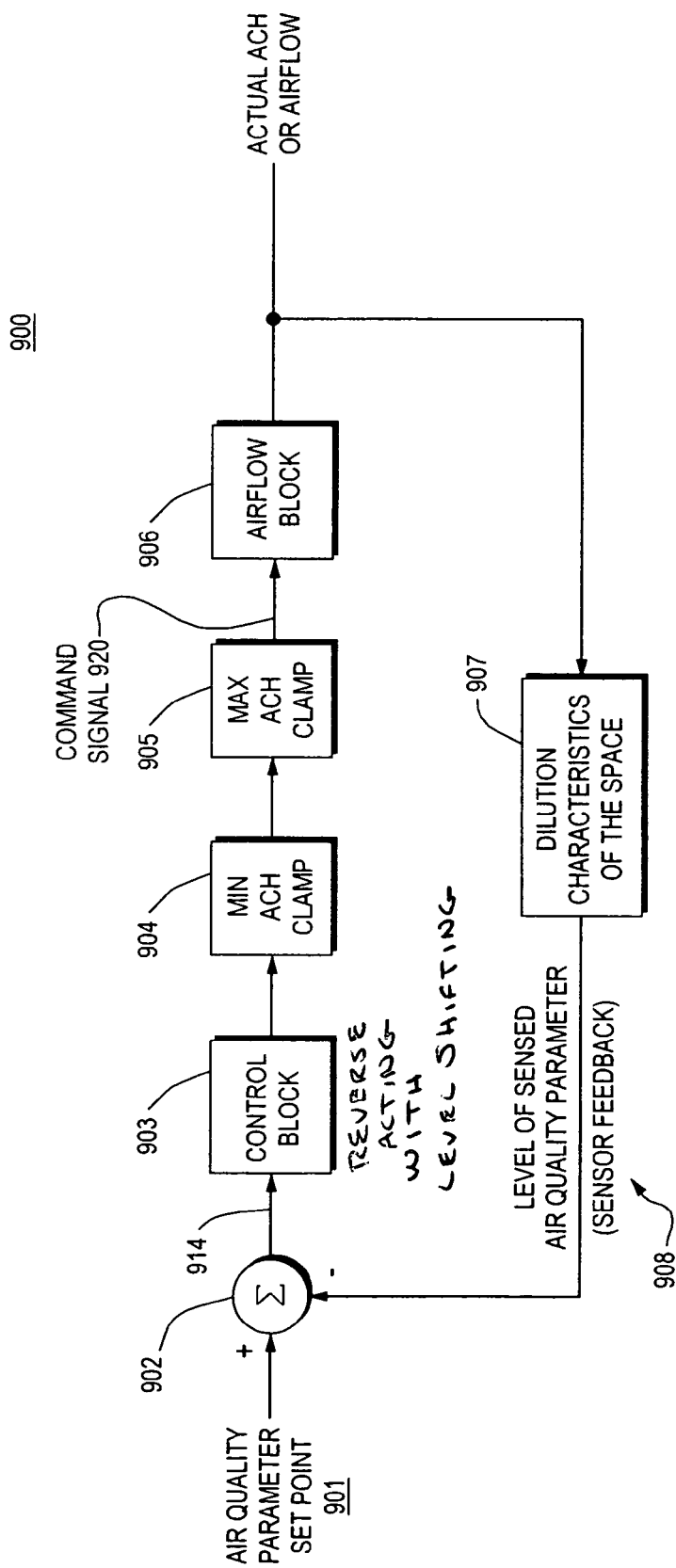
FIGS. 8A and 8B are diagrammed strategies for controlling the air change rate in a space or building environment using a closed loop system to provide dilution ventilation or outside air control by varying the supply air flow rate within the environment or the outside air into the building.
Figure 8B:
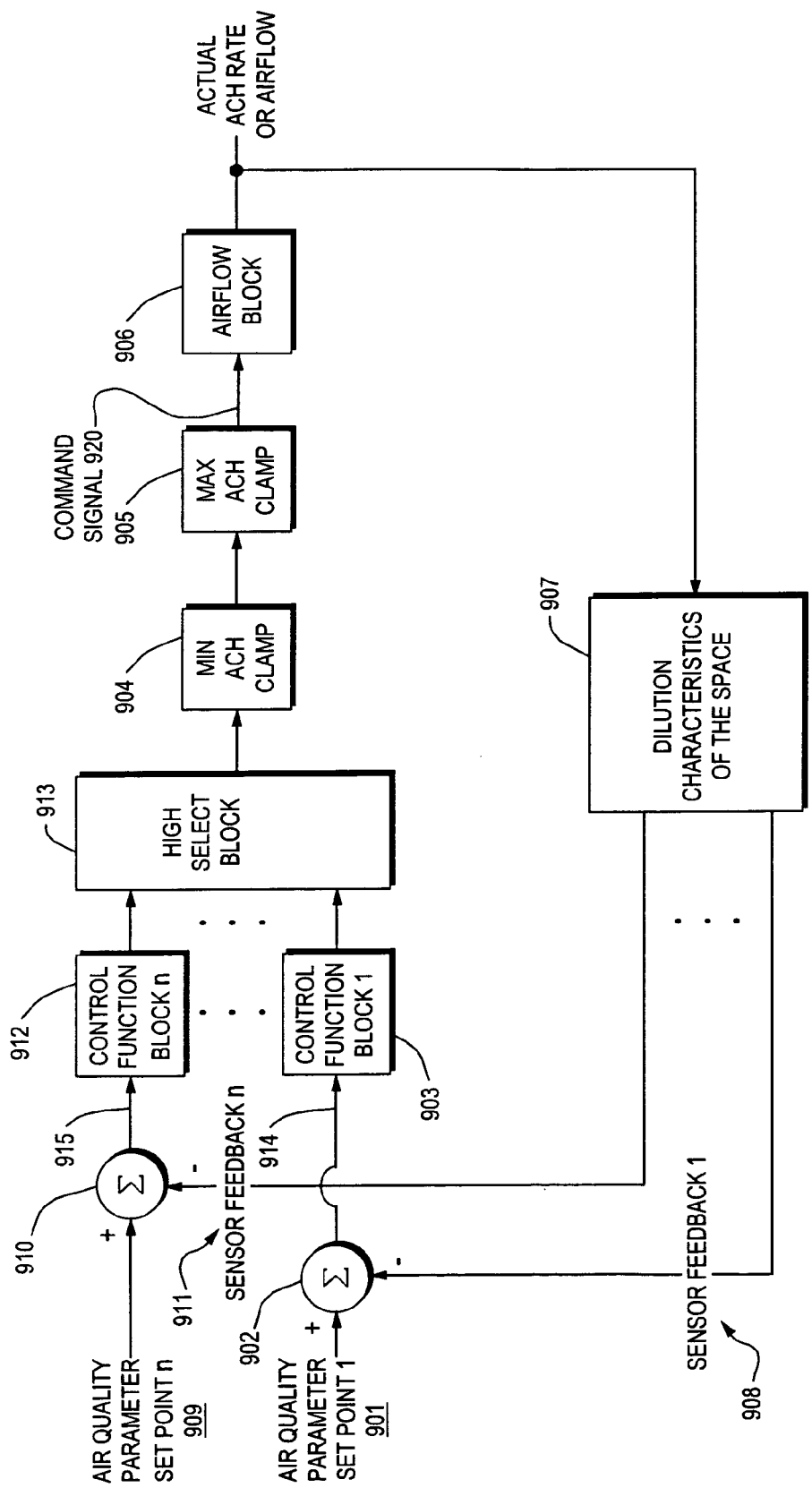

FIGS. 8A and 8B show a potential embodiment of the control logic and functionality of output control block 540A that incorporates a closed loop system 900 to provide dilution ventilation control by varying the air change rate or effectively the supply airflow rate within a environment, such as 20, in a continuous (or VAV) fashion within prescribed limits in order to prevent the level of a sensed air quality parameter, such as TVOC's for example or a blended air quality parameter signal as described above, from exceeding a prescribed value. Here, sensor feedback 908 which could be dilution ventilation feedback signal 538A of FIG. 4 is subtracted from air quality parameter set point 901, which represents the level of the sensed air quality parameter or blended set of parameters that system 900 is to control to, in order to (by error stage 902) create error signal 914. Error signal 914 is acted upon by control block 903 in order to create a term that is bounded by Min ACH Clamp block 904 and Max ACH clamp 905 in order to yield the command signal 920. The command signal 920 may represent the dilution ventilation command signal 31 of FIG. 4 or any other pertinent airflow command or control signal such as the outside airflow command signal 1075 depending on the nature and source of the sensed air quality parameter signal 908 and setpoint 901. Command signal 920 in FIG. 8 is also the command to air flow block 906, which may be composed of air flow controller 30 in FIGS. 1, 2, and 3 and the return and supply flow (42 and 52) that it controls. Alternatively, airflow block 906 could be another control block such as air handler damper controller 1213 in FIG. 9 and the associated dampers or air flow control devices 1068, 1070, and 1072 of FIG. 6 representing the control devices for air handler 1000's associated airflows of outside air 1007, exhaust air 1004, and recirculated air 1005. Also depicted in FIG. 8A is block 907, which represents the dilution characteristics of the environment. For those who are familiar with the art of control system design, 907 represents the transfer characteristics of the environment which in this case defines how the air flow rate of the environment under control relates to the value of the sensed air quality parameter 908. Here, error stage 902, reverse acting control block 903, Min ACH Clamp 904, and Max ACH clamp 905 may be implemented within output control block 540A or outside airflow controller block 1200 of FIGS. 6 and 9, or potentially within or partially within signal processing controller blocks 130, 210, 530, or 1130 of FIG. 1, 2, 4, or 6 respectively or within Building Control System 180.

Control block 903 may be implemented using any of a large number of control strategies known to those who are skilled in the art of control system design and may as an example include any combination of proportional control, proportional-integral control, proportional-integral-derivative control, feed forward techniques, adaptive and predictive control, and fuzzy logic strategies. One of the essential elements of control block 903 is that it provide the necessary reverse acting and level-shifting functions so that it may properly act upon error signal 914 (given the subtractive logic shown for error stage 902) in order to create a command signal 920 which can yield an increase in the environment's air flow rate at least for the condition where the sensor feedback 908 exceeds the air quality parameter set point 901. (Alternatively, the logic of 902 could be altered so that 901 is subtracted from 908.) As an example, air quality parameter setpoint 901 may be set to 1.5 ppm and the sensed air quality parameter may be, for example a blended signal created from sensing TVOC's (using, for example a photo-ionization detector—or HD sensor) and carbon dioxide. Control block 903 will be configured so that when sensor feedback 908 is less than setpoint 901 the output of 903 will be less than or equal to the minimum clamp value established by minimum ACH clamp block 904. 904 is a "high-select" block in that it will compare the value of the output of 903 to some minimum clamp value (4 ACH, for example) and present the larger of the two values to the next block 905. For example, if the output of 903 is 2 ACH and the minimum clamp value set in 904 is 4 ACH, the output of 904 will be 4 ACH. The output of 904 is presented to Max ACH clamp 905 which provides a "low-select" function in that it will compare the value of the output of 904 to a prescribed "max clamp" value (12 ACH, for example) and output the smaller of the two to air flow block 906. The way the system 900 works is that if there is some sudden increase in the level of the sensed air quality parameter (due to a spill of cleaning compounds, for example) above the air quality parameter setpoint 901 (set to 1.5 ppm TVOC's for example) the control block will (within the limitations of max clamp 905 set to 12 ACH, for example) increase command signal 920 to the value necessary to limit a TVOC concentration within the controlled environment to 1.5 ppm. In practice, set point 901 can be set to a value less than the TLV for the air quality parameter or blend of parameters to be sensed to insure that sustained concentrations will be limited to a steady-state value that is safe. Alternatively, air quality parameter set point 901 may have a dynamic value that adjusts based on the persistence of the air quality parameter monitored by 908.

FIG. 8B illustrates an alternate embodiment of system 900 that provides the same control functions as FIG. 8A, but for any number "n" of air quality parameters using individual air quality parameter feedback signals such as the outputs of 561a, 562A, 534A, 535A, or 536A of FIG. 4 vs. the approach of FIG. 8A that uses a blended air quality parameter feedback signal such as 538A of FIG. 4. With this approach, a dedicated error stage 902 and control function block 903 are provided for each sensed air quality parameter (1 through "n"), with the nth sensed air quality parameter's set point shown as signal 909 going to error stage 910 which has an output 915 that is processed by function block 912. The outputs from each control block, such as from control blocks 903 to 912, are presented to high select block 913, which passes the largest of the control terms from the control blocks to airflow block 906 as command signal 920. Using this approach, one can provide dilution ventilation control to an environment such as 20 based on a blended command signal 920 that is created from a plurality of air quality parameters, such as TVOC's, particles, and a host of other air quality parameters using individual setpoints such as 901 to 909 for each monitored air quality parameter as well as individual sensed air quality parameter feedback signals 908 or 911. Effectively FIG. 8B allows the individual control function blocks 912 be individualized for each air quality parameter which may be advantageous in some situations due to certain air quality feedback signals potentially requiring different control gain and stability settings that are best handled on an individual control loop basis vs. using one control loop and gain settings and a blended feedback signal. With the implementation of FIG. 8B the integration of the control loops at the high select block 913 creates a blended command signal 920. Additionally, for some situations block 913 may be implemented as a summation vs. a high select block where each of the inputs to block 913 are scaled as necessary to allow the signals to be properly weighted and summed with respect to each other.

Using the systems of FIG. 1, 2, 6, or the networked photonic sampling system, there are several beneficial control implementations and methods that can be implemented to solve problems that occur when trying to create and use blended or composite air quality parameter based signals for use in the monitoring and control of building systems such as HVAC systems. One application of these signals is in the control of outside air into a building or similarly controlling the amount of dilution ventilation or outside air provided into a space. For example, the outside air that is being brought into the building may become slightly or significantly contaminated by one or more air contaminants. Such air contaminants could include carbon monoxide from auto or truck exhaust or from re-entrainment of furnace or boiler exhaust, high levels of outdoor particulates, TVOC's that could be re-entrained from nearby exhaust stacks, or other outdoor sources of air contaminants. If these air contaminants are not filtered out and pass into the supply air that is being fed into the rooms it could trigger the dilution ventilation controls to increase the supply air flows and or the outside air flow from the outside air intakes inappropriately. Similarly, the increase in supply air contaminants may not be high enough to trigger increased supply air or outside air flow commands by itself, but added to existing air contaminant levels in the room or building it may make the system overly sensitive to low or moderate air contaminant levels originating from within the room or building. Both of these problems can produce potentially runaway results since the control action of increasing supply or outside air which contains air contaminants only serves to increase the level of the particular air contaminant within the room or building. This can drive the supply or outside airflow levels even higher until no matter whether a two state, three state, or VAV approach is used the supply airflow into the room or the outside airflow into the building will eventually be commanded to its maximum level if the outside air or supply system contamination is high enough. Since the supply system airflow potentially feeds many rooms, potentially all of these rooms could be pushed to their maximum flows or else the amount of outside air being drawn into the building could reach potentially as high as 100% outside air. This could result in the airflow capacity and or the heating and cooling capacity of the supply system being exceeded with potential resultant reductions of flow into the room spaces and also potential loss of temperature control of these spaces if the temperature of the conditioned supply air can not be appropriately controlled due to an excessive amount of outside air being drawn into the building.

Alternatively in a building that uses return air such as is shown and implemented with the air handling unit 1000 in FIG. 6, a high level of contaminants in one space may be recirculated into other spaces through the return and then supply air. The correct action in this case would not be to increase room supply air in individual rooms but to instead appropriately increase outside air to dilute the entire building including the space that is the source of contaminants.

One exemplary control approach to solve these problems is to use a differential measurement technique. In this approach an outside air or supply air measurement is subtracted from room air measurements to create differential measurements of the various air contaminants of interest vs. either outside air or the supply air. Thus, if the outside or supply air has an increase in particles, CO, TVOC's, etc., the air quality of the room air will be evaluated against sources of air contaminants in the room only since the effect of the supply air sources will be subtracted out. Effectively, we are concerned here not with the absolute air quality of the room air but whether it is being made worse by sources in the room or space only, since increasing the supply or outside air will not make the room air cleaner if the supply or outside air is the source of the air contaminant.

For example, as mentioned previously, we first start with air contaminant measurements of the air in for example space 20A using for example room sampling location 23A, return air duct sampling location 43A, and or room sensor 27A in FIGS. 1 and 2. Alternatively as shown in FIG. 6 building level measurements such as from air handing unit 1000's return duct air sampling location 1031, and or the return duct sensor 1021 selected to sense an air contaminant vs. temperature, may also be used. In this exemplary approach a reference measurement of the air contaminants is next made based on the following mentioned circumstances at either 1) the outside air using for example air sampling location 63 in FIG. 1 or 2, or the air sampling location 1033 in FIG. 6, or 2) the supply air using for example the supply duct air sampling location 53B in FIG. 1 or 2, or the air handler 1000 supply duct air sampling location 1037 in FIG. 6. The specific location to be sensed, either one measuring the outside air or measuring the supply air, varies based on the type of air handling system and the parameters of interest. For example, if the spaces are receiving 100% outside air directly from outdoors with no return air, then a measurement of either supply air or outside air from within the outside air duct 60 of FIG. 1 or from outside air duct sampling location 1033 of FIG. 6 will provide accurate results for at least gas or VOC measurements. However, when at least particle measurements are a sensed air contaminant of interest, it is important that the reference measurement of the air contaminants be taken at a location downstream from all the air filters and fan systems of the air handling unit such as at the supply air duct sampling locations 1037 or 53B mentioned above. This requirement is due to the impact of supply air handling unit filters such as prefilter 1016 and filter 1008 in FIG. 6 that changes the particle readings between a direct outside air measurement and one of the supply air after the filters. Consequently, for this latter situation and these reasons, the reference measurement should not be taken directly from an outside air measurement.

Furthermore, if return air from other areas is mixed with outside air to produce the supply air as is shown with the air handling unit 1000 in FIG. 6, then the use of a downstream supply duct airflow reference measurement instead of a direct outside air reference measurement as a reference for space or area contaminant measurements is also necessary with a location at least after where the outside air and return air become well mixed. This is the case for any air contaminant measurement involving return air systems even gases since the mixing of the outside and return air will potentially produce a different level of contaminant in the supply duct vs what would be seen directly outside. The use of only one supply or outside air duct measurement should be sufficient for all the spaces fed from a single air handler or main supply duct since all the supply air flowing into these spaces from the same air system should have similar characteristics and air contaminant values.

If on the other hand air contaminant measurements of building supply air or building return air are being used to help control the amount of outside air brought into the building then the appropriate reference measurement should be taken from outside air measurements and not from supply air measurements.

The next step in this exemplary approach involves taking each pair of air contaminant measurements (space or building air and outside or supply air) and converting them into a set of differential measurements by subtracting the reference outside or supply air contaminant measurement from the space air contaminant measurement, or vice versa if more convenient to do so. An example of an embodiment to perform this is the subtraction block 37 of FIG. 5 where a supply or outside air measurement of for example TVOC's would be applied to the minus (−) input of the subtraction block and the space or return duct air contaminant measurement of TVOC's would then be applied to the positive (+) input. The output would then be the differential measurement of TVOC's for that space. Other methods of subtracting these air contaminant measurements for software variables in a computerized control system for example or for other implementations would be known to those well skilled in the art.

The individual differential air contaminant measurements would then be treated in the same manner described previously for the non-differential room air measurements and thus would be used, for example, individually or combined and then compared or analyzed by signal processing controller block 130, 210, 530 or 1130 of FIG. 1, 2, 4 or 6 respectively to create air quality parameter feedback signals 538A or 1075 that can be further operated upon by for example output command block 540A or outside airflow controller 1200 respectively to yield command signals 31 to vary the supply airflow into space 20 and command signal 1075 that would be used or the outside airflow into the building.

The shared sensor multipoint air sampling system embodiments of FIG. 1, 2, or 6 are preferred embodiments for this differential measurement control concept since the measurement of the supply or outside air and the space air measurement can be performed with the same sensor within a reasonably short period of time such as 5 to 30 minutes. As a result many sensor errors are eliminated since they cancel out when subtracting the two measurements. Consequently, very accurate differential measurements can be made even when the increase in air contaminants in the room although important is relatively small compared to a potentially high source level of outside air or supply air contaminants. As a result these high outside or supply background levels do not substantially decrease the resolution or accuracy of the measurement of any air contaminant sources within the environment spaces.

Another preferred control approach that can be used with the implementation of FIG. 1, 2 or 6 relates to a situation where a high level of supply or outside air contaminant may be present, yet the differential room air signal mentioned previously indicates that there are not substantive sources of air contaminants in the space. In this situation the absolute level of air contaminants in the space may be high enough to trigger an increased dilution level, but the differential signal correctly indicates that increasing the supply air is not appropriate. In this situation, since the source of the air contaminant is the supply air, it may be advantageous to reduce the supply air via supply air control device 51 and or the outside air through the outside air control damper 1067 until the outside or source air contains a lower level of air contaminants.

One embodiment of this control approach consists of making one or more air contaminant measurements in the supply duct 50B, outside air intake duct 60, or air handler outside air duct sampling location 1033 as mentioned previously. These one or more air contaminant measurements can then be combined or used individually and then compared or analyzed by signal processing controller block 130, 210, 530 or 1130 of FIG. 1, 2, 4 or 6 respectively to determine if these signals exceed appropriate trigger levels such as those used for the environment spaces 20. If these trigger levels or appropriate trigger conditions are met, then blocks 130, 210 or 1130 can be used to reduce the supply and or outside air flow by one of several approaches. For example to reduce room supply flow, the temperature control output 93 in FIG. 3 of the temperature control block 90 can be completely overridden and effectively disabled by a command output from signal processing controller blocks 130 or 210 so that the supply flow will become controlled solely by the flow commanded by the dilution ventilation command 31 which would be reduced to a low level. For example, to reduce building outside airflow the outside air damper 1067 of air handler unit 1000 could be commanded by signal processor controller 1130 to a lower flow rate representing the minimum required flow rate for occupancy, versus a potentially higher rate for free cooling with an economizer.

One particularly useful blended air quality parameter measurement that can be performed with this invention relates to enthalpy measurements. With reference to this, a hygrometer is a device used to make moisture measurements, and typically provides a voltage, current, or digital output that is representative of the moisture content of the air or other gas that is sampled. The fundamental measurement made by a hygrometer is typically dew point (or condensation) temperature or may be presented in terms of concentration, such as parts per million—ppm—or parts per thousand—ppt—, or some other suitable system of units. Also, it is quite common for commercially available hygrometers to calculate other psychrometric properties that may require a simultaneous measurement of a second property of the sensed gas, such as temperature, in order to derive the desired property, such as enthalpy and relative humidity, as well as other properties. Also, if absolute pressure is known, the hygrometer's moisture measurement can be used to derive humidity ratio, which is also provided by some commercially available hygrometers. For purposes of this invention, a hygrometer may be based on any of various technologies known to those familiar with the art of moisture measurement. These technologies include but are not limited to: chilled mirror hygrometers, infrared-based moisture analyzers, surface acoustic wave (SAW) technology, aluminum oxide sensors, and sensors that combine an RH sensing device with a temperature sensor in order to derive a dew point temperature, moisture concentration, or other suitable measurement of moisture content from the sensed air or other gas being sensed. For example, sources of some of these types of instruments include a chilled mirror hygrometer that can be provided by Edgetech Moisture and Humidity Systems of Marlborough, Mass. or an infrared-based moisture analyzers such as the LICOR 840 unit that can be obtained from LICOR Biosciences corporation.

When a derived psychrometric property such as enthalpy, RH, and other temperature or pressure dependent properties is measured by such hygrometer devices, the accuracy of the derived parameters (RH, enthalpy, etc. . . . ) is highly dependent on the accuracy of the local measurement of temperature or pressure that is simultaneously made by the device. Therefore, when applying such hygrometer devices to multipoint sampling systems, only the fundamental dew point temperature or moisture concentration measurement that it provides is usable as most of the derived psychrometric properties (such as RH and enthalpy) will actually be altered as an air sample is transported from a sampled location to the shared sensor location 220 (FIG. 2) of the multipoint sampling system, due to (for example) the difference in temperature between the sampled location and the shared sensor location 220.

The formulation of an enthalpy or other psychrometric property signal can also be derived from psychrometric charts that are well known in the art. As an example, U.S. Pat. No. 4,672,560, which is incorporated herein by reference, discloses an exemplary enthalpy calculator.

One common way to compute RH from dew point temperature and ambient temperature involves, for example, an interpretation of the Clausius-Clapeyron equation for vapor pressure as set forth in Equation (1) below:

$$RH = 100 * E/E_s = 100 \left[ \frac{6.11 e^{5321\left(\frac{1}{273} - \frac{1}{T_a}\right)}}{6.11 e^{5321\left(\frac{1}{273} - \frac{1}{T_D}\right)}} \right] \quad \text{Eq. 1}$$

where, E=Vapor Pressure, $E_S$=Saturation Vapor Pressure, $T_A$=Ambient Temperature in Kelvins, and $T_D$=Saturation or Dew Point Temperature in Kelvins. Additionally, as is known to those familiar with the art of psychrometrics, there are numerous other approximations that may be used to calculate vapor pressure and saturation vapor pressure when temperature and dew point temperature are known, from which RH and other psychrometric properties, such as enthalpy, can be calculated.

By inspection of Equation (1), one can see that relative humidity is not only dependent on dew point temperature $T_D$, but that it is also dependant on ambient temperature $T_A$. For example, using this equation, we can see that for a given dew point temperature 51 degF (for example) if an air sample is taken from a location at 70 degrees F. by an air sampling system, and in the process of transport to shared sensors 220 (FIG. 2) containing the hygrometer the sample's temperature increases to 75 degrees F., the RH of that sample will change from about 51% RH to about 43% RH, which is significant when making such measurements. A similar problem exists when making remote measurements of other psychrometric properties.

In one aspect of this invention, a multipoint air sampling system includes a hygrometer included as one of its shared sensors 220 (FIG. 2) in a common sensor suite, which sensor's moisture measurement for each sampled location (for example, 20A, 20B, and 20C) is combined with a local temperature measurement (such as 25A) made from each sampled space to generate a signal (such as 181 which connects to a BAS, or signal 571A), representing a temperature dependent psychrometric property such as for example enthalpy or relative humidity for each sampled space 20A, 20B, 20C.

A multipoint air sampling system may include a hygrometer in the sensor suite that can be used in combination with local discrete temperature and even pressure sensors at sensed locations to determine both absolute humidity and temperature for the sensed locations to calculate a blended air quality parameter signal representing relative humidity, enthalpy, humidity ratio, and other psychrometric properties. One important benefit of this arrangement when applied to RH sensing, is that it provides a significant improvement over conventional systems using distributed RH sensors, which tend to drift significantly over time. This is particularly the case when making RH measurements within a plenum or duct work used in a building's ventilation system. For example, if a hygrometer is incorporated with the shared sensors 220 (FIG. 2), the output temperature sensor 27B (FIG. 2) located in duct 50B can be combined with moisture measurements obtained from sensed location 53B in order to proved a highly accurate and drift stable measurement of RH and other temperature dependent psychrometric properties from duct SOB. This has great advantages over commercially available duct-mounted RH sensors which tend to be unreliable due to, among other things, fowling related to the particulate matter exposure of these sensors when placed in an air flow stream. Also these discrete sensors tend to be expensive due to the cost of the sensor element and the power supply and mechanical housing required.

Similarly, highly accurate and stable enthalpy measurements can be made according to the teachings of this invention which provides a substantial improvement over conventional means of making such measurements. This is particularly important to applications relating to the control of outside air (such as economizer applications), and other air handler control applications.

An example of the creation and use of these blended enthalpy measurements plus other blended air quality parameter measurements for outside air control purposes is shown in FIG. 9 that shows a potential implementation for the logic and functions of the outside airflow controller block 1200 from FIG. 6. In this diagram an enthalpy calculation for return air 1001 is performed by the return enthalpy block 1205 using some of the psychrometric relationships discussed previously and the air quality parameter measurements of return air dewpoint or absolute humidity 1201 plus the return air temperature 1202. These measurements are taken from sampling location 1031 and duct sensor 1021 respectively and processed by the signal processing controller block 1130 from FIG. 6. Similarly an outside air enthalpy measurement is made by outside air enthalpy block 1206 using outside air dewpoint or absolute humidity signal 1203 and outside air temperature signal 1204. These measurements are taken respectively from air sampling location 1033 and duct sensor 1023. The two enthalpy signals outputted from blocks 1205 and 1206 are subtracted from each other by subtraction block 1207 either as shown or with return air enthalpy subtracted from outside air enthalpy signal. The resultant differential enthalpy signal is used in an economizer controller 1208 as are commercially available and known to those skilled in the air that can generate an outside air flow command to bring in more outside air when it would be less costly to do that vs. cooling return air. A manufacture of commercial economizer controllers is Honeywell.

The free cooling outside airflow command from economizer controller 1208 can then be further scaled and offset by function block 1209 and then acted upon by low select comparator or override block 1210. The purpose of this block is to override and reduce the free cooling outside air command from the economizer 1208 when the outside air is contaminated to a level where it would be better not to increase outside air if possible. To implement this function outside air contaminant measurements can be made and combined and used by the low select comparator. This is shown for example with outdoor air quality parameter signals 1221, 1223, and 1225 representing outdoor levels of particles, carbon monoxide, and TVOC's respectively. These signals are then compared to their respective threshold signals or setpoints 1220, 1222, and 1224. Comparators 1231, 1233, and 1235 individually compare these outdoor air contaminant signals and produce output signals that go high in either a two state, multi-state or continuously variable manner based on the difference of that threshold to the air quality parameter signal. These compared signals are then provided to function blocks 1232, 1234, and 1236 which can scale and offset or apply any other appropriate processing of these signals so they can be used by low select comparator 1210 to override either completely or on a partial basis the scaled output of the economizer. Equivalently the outdoor air quality parameter signals could be combined and blended into a blended outdoor air quality parameter signal and one comparator could be used to create the override signal. Otherwise low select comparator 1210 combines and uses the individual signals. The output of the comparator block 1210 is then scaled or modified by another function block 1211 so it can be on the same scale or appropriate to be high selected with a signal representing the amount of outside air necessary to provide for the amount of occupancy in the building based on CO2 measurements as well as enough outside air to properly dilute any air contaminants that happen to be generated in the building.

The creation of this combined dilution and occupancy based outside air command signal begins with air quality parameter measurements from the signal processing controller 1130 that may be based on de-multiplexed shared sensor measurements or local sensor readings. For example, the diagram indicates a potential setup using the measurements from two rooms, 20A and 20 B, and two air quality parameter measurements for each room namely CO2 that is being used to determine the outside air volume requirements for occupancy and TVOC's that is representative of an air contaminant measurement to determine the amount of outside air required for diluting these air contaminants. Alternatively, other air contaminants could be used as well as multiple air contaminants that could be used to create a blended air contaminants signal. Furthermore as mentioned above it is preferred to use differential measurements of air contaminants vs the appropriate reference. When using room air measurements for controlling outside air into the building the appropriate reference is outside air measurements. Therefore outdoor TVOC signal 1225 is subtracted from Room 20A TVOC signal 1227 by subtraction block 1237. Similarly outside TVOC reference 1225 is subtracted from Room 20B TVOC signal 1229 by subtraction block 1239. As has been mentioned before any of these subtractions or the ones for CO2 can be performed the other way around, with one signal being subtracted from the other or vice versa. These difference measurements produce differential air contaminant signals 1241 for room 20A and 1243 from room 20B and are further processed by scale and offset blocks 1245 and 1247 respectively. These rooms or other rooms selected for either air contaminant measurement or CO2 occupancy measurements are typically chosen because they are considered "critical zones" having the potential for either high occupancy or high levels of air contaminants.

For information on the occupancy requirements for outside air CO2 is used as a means to measure occupancy and the amount of outside air delivered to a space as has been mentioned previously. To perform the appropriate measurement a differential measurement of CO2 is also desired since this difference vs. the absolute level of CO2 in a space is what occupancy is directly based on. Therefore outdoor air CO2 signal 1226 is subtracted from room 20A CO2 signal 1228 in subtraction block 1238 to generate differential CO2 signal 1242 that is scaled and offset by scaling block 1246. Similarly outdoor air CO2 signal 1226 is subtracted from room 20B CO2 signal 1230 in subtraction block 1240 to generate differential CO2 signal 1244 that is scaled and offset by scaling block 1248. The respective scaled differential air contaminant signals can now be combined or blended in numerous ways based on the desired control requirements. For example these signal can be high selected which is preferred, or else they can be added together. One example is shown with the room 20B where the differential CO2 and TVOC signal are combined by blend function block 1249 to generate one blended air quality parameter signal for that room. Room 20A's signal are shown used individually but are then high selected or combined in special function control 1250 along with the blended signal from room 20B. The output of special function control 1250 is a flow command signal that is high selected against the modified free cooling signal to generate the final command signal for outside air 1075. Additionally, air handler damper controller block 1213 can be used to create the actual damper control signals 1068, 1070 and 1072 corresponding to outside air, exhaust air, and recirculated air respectively for the air handler 1000 potentially using feedback of outside airflow volume from outside airflow measurement signal 1080.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A system for monitoring air quality conditions and controlling air flow in an environment that includes an airflow control device that controls at least one airflow volume, the system comprising:

a multipoint air sampling system comprising one or more sensors that detect one or more of air comfort parameters or air contaminants, the sensors generating output signals indicative of the level of the detected air comfort parameters or air contaminants, wherein at least one of the sensors is a shared sensor that senses contaminants in the air that has been collected from a plurality of separate locations, the separate locations including an at least partially enclosed area and at least one location containing outside air or supply air;

a signal processing controller that receives the sensor output signals and in response generates one or more blended air quality parameter signals and provides one or more of such blended air quality parameter signals to the airflow control device, to control at least the supply airflow volume provided to the at least partially enclosed area, wherein at least one of the blended air quality parameter signals comprises a differential air quality parameter signal that represents the magnitude of the difference between the sensed value of at least one air contaminant in the at least partially enclosed area and the sensed value of the same air contaminant in one of the outside air or the supply air, the signal processing controller comprising one or more demultiplexers that develop separate signals representing each sensed air contaminant in each of the separate locations;

wherein the signal processing controller generates signals that cause the airflow control device to increase the supply air volume when the differential air quality parameter signal is greater than a threshold signal value or exhibits a predetermined signal pattern comprising a rapid increase in the sensed air contaminant.

2. The system of claim 1 wherein one or more of the sensors is selected from a group of sensors consisting of electro-chemical, optical, infrared absorption, photo-acoustic, polymer, variable conductivity, flame ionization, photo-ionization, solid state, mixed metal oxide, ion mobility, surface acoustic wave, and fiber optic.

3. The system of claim 1 wherein the air contaminants comprise one or more contaminants selected from a group consisting of: chemical, biological, and radiological composition elements; particles having a diameter between about 0.01 microns to about 100 microns; carbon monoxide; smoke; aerosols; formaldehyde; NOX; SOX; hydrogen sulfide; chlorine; methane; hydrocarbons; ammonia; refrigerant gases; radon; ozone; radiation; biological terrorist agents; chemical terrorist agents; toxic gases; mold; and bacteria.

4. The system of claim 1 wherein the air comfort parameters comprise one or more parameters selected from a group consisting of: temperature, humidity, relative humidity, dewpoint temperature, absolute humidity, wet bulb temperature, and enthalpy.

5. The system of claim 1 further comprising a local sensor that senses temperature, and wherein at least one of the shared sensors senses one of a group of parameters including absolute humidity and dewpoint temperature and senses in the area where the local temperature sensor is located, and wherein at least one blended air quality parameter signal represents either the relative humidity, wet bulb temperature or enthalpy value of the area sensed.

6. The system of claim 5 further comprising:

an air handling unit where a percentage of the return air from the at least partially enclosed area is mixed with a percentage of outside air to create the supply air to be provided to the at least partially enclosed area; and wherein the signal processing controller uses the local temperature sensors to sense both return and outside air temperature of said air handling unit and also uses one of the shared sensors to generate a differential enthalpy signal equal to the blended air quality parameter signal represented by the difference between the enthalpy values of the air handler's return air and outside air.

7. The system of claim 6 further comprising:
an economizer controller for the air handling unit that uses the differential enthalpy signal to at least partially increase outside airflow when the enthalpy value of outside air is less than the enthalpy value of the return air; and
wherein the airflow control device comprises an outside airflow controller that is used to override the operation of the economizer controller when the value of at least one sensed air contaminant in the outside air is greater than a threshold signal value or exhibits a predetermined signal pattern.

8. The system of claim 7 wherein the outside airflow controller is also used to increase the amount of outside air when the value of the differential enthalpy signal is greater than a threshold signal value or exhibits a predetermined signal pattern.

9. The system of claim 1 wherein the signal processing controller generates signals that cause the airflow control device to at least partially decrease the outside air volume into the at least partially enclosed area when the value of at least one sensed air contaminant in the outside air is greater than a threshold signal value or exhibits a predetermined signal pattern.

10. The system of claim 1 wherein the signal processing controller creates a dilution ventilation command signal.

11. The system of claim 1 further comprising a local occupancy sensor.

12. The system of claim 1 wherein the signal processing controller generates signals that cause the airflow control device to at least partially decrease the supply air volume when the level of at least one sensed air contaminant in the supply air is greater than a threshold value or exhibits a predetermined signal pattern.

13. The system of claim 1 wherein the signal processing controller is used to at least partially control the outside air into a building and at least partially increase the outside air volume into the building, when the differential air quality parameter signal is greater than the threshold signal value or exhibits the predetermined signal pattern.

14. The system of claim 13 further comprising:
an air handling unit where a percentage of the return air from an at least partially enclosed area down to and including 0% is mixed with a percentage up to and including 100% of outside air into the building to create the supply air to be provided to the at least partially enclosed area; and
wherein the signal processing controller generates signals that cause the airflow control device to at least partially increase the outside air volume into the building through the air handling unit, when the differential air quality parameter signal is greater than the threshold signal value or exhibits the predetermined signal pattern.

15. The system of claim 13 wherein the value of the output signal of a local or shared sensor is used to at least partially change the threshold signal value or the predetermined signal pattern.

16. The system of claim 1 wherein the signal processing controller scales the air quality parameter signals so that they are on the same relative scale.

17. The system of claim 1 wherein at least one of the sensors senses carbon dioxide and at least one of the sensors senses a different air contaminant, and wherein the output signals from such sensors are used by the signal processing controller to create at least one blended air quality parameter signal, and wherein the signal processing controller uses the blended air quality parameter signal to create a dilution ventilation command signal that is communicated to the airflow control device to at least partially control the at least one airflow volume.

18. The system of claim 1 wherein the value of the output signal of the shared sensor is used to at least partially change the threshold signal value or the predetermined signal pattern.

* * * * *